(12) United States Patent
Motomura et al.

(10) Patent No.: US 9,040,717 B2
(45) Date of Patent: May 26, 2015

(54) PYRAZOLE-AMIDE COMPOUNDS AND PHARMACEUTICAL USE THEREOF

(71) Applicant: JAPAN TOBACCO INC., Tokyo (JP)

(72) Inventors: Takahisa Motomura, Takatsuki (JP); Gakujun Shomi, Takatsuki (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 14/210,746

(22) Filed: Mar. 14, 2014

(65) Prior Publication Data

US 2014/0296315 A1    Oct. 2, 2014

Related U.S. Application Data

(60) Provisional application No. 61/791,164, filed on Mar. 15, 2013.

(30) Foreign Application Priority Data

Mar. 15, 2013  (JP) ................................. 2013-053195
Jun. 18, 2013  (JP) ................................. 2013-127318

(51) Int. Cl.
  *C07D 231/12*  (2006.01)
  *A61K 31/415*  (2006.01)

(52) U.S. Cl.
  CPC .................................... *C07D 231/12* (2013.01)

(58) Field of Classification Search
  None
  See application file for complete search history.

(56) References Cited

U.S. PATENT DOCUMENTS

| | | | |
|---|---|---|---|
| 7,098,241 B2 | 8/2006 | Grossmann et al. | |
| 7,485,634 B2 | 2/2009 | Martin et al. | |
| 7,585,837 B2 | 9/2009 | Shechter et al. | |
| 7,674,795 B2 | 3/2010 | Mailliet et al. | |
| 8,133,992 B2 | 3/2012 | Martin et al. | |
| 8,343,910 B2 | 1/2013 | Shechter et al. | |
| 8,343,994 B2 | 1/2013 | Motomura et al. | |
| 8,735,350 B2 | 5/2014 | Shechter et al. | |
| 2004/0023947 A1 | 2/2004 | Martin et al. | |
| 2006/0171920 A1 | 8/2006 | Shechter et al. | |
| 2008/0153837 A1 | 6/2008 | Mailliet et al. | |
| 2008/0200551 A1 | 8/2008 | Yamada et al. | |
| 2009/0326218 A1 | 12/2009 | Martin et al. | |
| 2010/0041867 A1 | 2/2010 | Shechter et al. | |
| 2010/0240634 A1 | 9/2010 | Motomura et al. | |
| 2012/0035196 A1 | 2/2012 | Negoro et al. | |
| 2013/0116175 A1 | 5/2013 | Shechter et al. | |
| 2013/0274240 A1 | 10/2013 | Motomura et al. | |
| 2014/0121352 A1 | 5/2014 | Shechter et al. | |
| 2014/0296316 A1 | 10/2014 | Motomura | |
| 2015/0018403 A1 | 1/2015 | Motomura et al. | |
| 2015/0025120 A1 | 1/2015 | Motomura et al. | |

FOREIGN PATENT DOCUMENTS

| | | |
|---|---|---|
| WO | 03/011844 A2 | 2/2003 |
| WO | 03/099821 A1 | 12/2003 |
| WO | 2004/089280 A2 | 10/2004 |
| WO | 2005/080322 A1 | 9/2005 |
| WO | 2006/123061 A2 | 11/2006 |
| WO | 2010/041748 A1 | 4/2010 |
| WO | 2010/123016 A1 | 10/2010 |

OTHER PUBLICATIONS

Hörig et al., J. Translational Med. 2:44 (2004).*
Roche, et al., Cell. Mol. Life. Sci., 7-8:830 (2007).*
Karpov, V.M. et al., "Skeletal transformations of perfluoro-1-phenylindan under the action of antimony pentafluoride," Journal of Fluorine Chemistry, vol. 107, No. 1, pp. 53-57 (2001).
Alcher, T. et al., "(R)-3,3,3-Trifluoro-2-hydroxy-2-methyl-propionamides Are Orally Active Inhibitors of Pyruvate Dehydrogenase Kinase", Journal of Medicinal Chemistry, vol. 42, No. 15, pp. 2741-2746 (1999).
Bebernitz, G.R. et al., "The Effect of 1,3-Diaryl-[1H]-pyrazole-4-acetamides on Glucose Utilization in ob/ob Mice", Journal of Medicinal Chemistry, vol. 44, No. 16, pp. 2601-2611 (2001).
International Search Report issued in International Patent Application No. PCT/JP2014/056825 (Apr. 8, 2014) (4 pages).
USPTO Office Action for U.S. Appl. No. 14/318,887 dated Feb. 13, 2015.
USPTO Office Action for U.S. Appl. No. 14/318,931 dated Feb. 24, 2015.
Preliminary Amendment in U.S. Appl. No. 14/484,666, filed Apr. 10, 2015.

* cited by examiner

*Primary Examiner* — Michael Barker
(74) *Attorney, Agent, or Firm* — Fitzpatrick, Cella, Harper & Scinto

(57) ABSTRACT

A compound represented by the following formula:  [I]

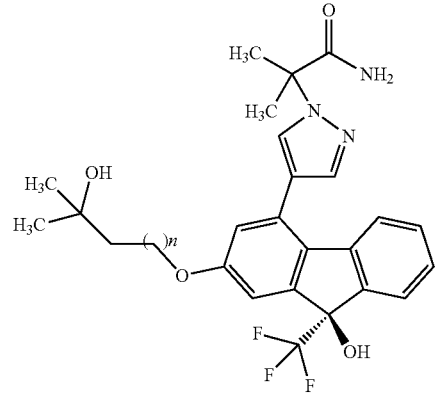

wherein n is 1 or 2,  [II]

-continued
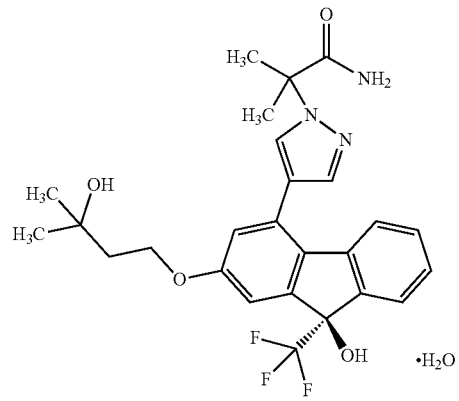
[IIh]
or
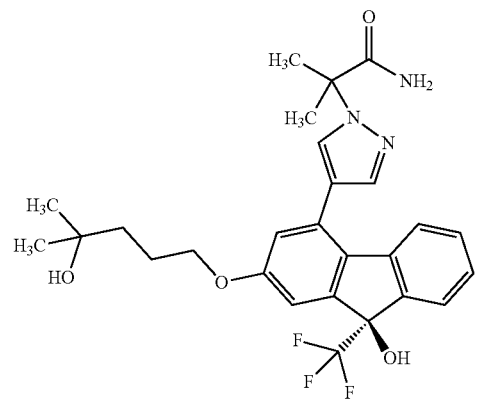
[III]
or a pharmaceutically acceptable salt thereof, and a pharmaceutical use thereof.
16 Claims, 2 Drawing Sheets

PYRAZOLE-AMIDE COMPOUNDS AND PHARMACEUTICAL USE THEREOF

TECHNICAL FIELD

The present invention provides a pyrazole-amide compound and a pharmaceutical use thereof. More particularly, the present invention relates to a pyrazole-amide compound or a pharmaceutically acceptable salt thereof having a pyruvate dehydrogenase kinase (hereinafter to be abbreviated as PDHK) inhibitory activity, a pharmaceutical composition containing the same, a prophylactic or therapeutic agent containing the same for diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension, or Alzheimer disease, and the like.

BACKGROUND ART

In tissues, for reactions using energy such as biosynthesis, active transport, muscle contraction and the like, the energy is supplied by hydrolysis of adenosine triphosphate (ATP). ATP is produced by oxidation of metabolic fuel which yields much energy, such as glucose and free fatty acids. In oxidative tissues such as muscle, ATP is mostly produced from acetyl-CoA that enters citric acid cycle. Acetyl-CoA is produced by oxidation of glucose via glycolytic pathway or β oxidation of free fatty acid. An enzyme that plays a pivotal role in controlling acetyl-CoA production from glucose is pyruvate dehydrogenase (hereinafter to be abbreviated as PDH). PDH catalyzes reduction of nicotinamide adenine dinucleotide (NAD) to NADH, simultaneously with oxidation of pyruvic acid to acetyl-CoA and carbon dioxide (e.g., non-patent documents 1, 2).

PDH is a multienzyme complex consisting of three enzyme components (E1, E2 and E3) and some subunits localized in mitochondrial matrix. E1, E2 and E3 are responsible for decarboxylation from pyruvic acid, production of acetyl-CoA and reduction of NAD to NADH, respectively.

Two classes of enzyme having regulatory function bind to PDH. One is PDHK, which is a protein kinase having specificity to PDH. The role thereof is to inactivate E1α subunit of the complex by phosphorylation. The other is PDH phosphatase, which is a specific protein phosphatase that activates PDH via dephosphorylation of E1α subunit. The proportion of PDH in its active (dephosphorylated) state is determined by the balance of kinase activity and phosphatase activity. The kinase activity is regulated by the relative concentration of metabolic substrates. For example, the kinase activity is activated by an increase in NADH/NAD, acetyl-CoA/CoA and ATP/adenosine diphosphate (ADP) ratios, and inhibited by pyruvic acid (e.g., non-patent document 3).

In the tissues of mammals, 4 kinds of PDHK isozymes are identified. Particularly, PDHK2 is expressed in a wide range of tissues including the liver, skeletal muscles and adipose tissues involved in glucose metabolism. Furthermore, since PDHK2 shows comparatively high sensitivity to activation by increased NADH/NAD or acetyl-CoA/CoA and inhibition by pyruvic acid, involvement in a short-term regulation of glucose metabolism is suggested (e.g., non-patent document 4).

In addition, PDHK1 is expressed in large amounts in cardiac muscle, skeletal muscle, pancreatic β cell and the like. Furthermore, since expression of PDHK1 is induced via activation of hypoxia inducible factor (HIF) 1 in ischemic state, its involvement in ischemic diseases and cancerous diseases is suggested (e.g., non-patent document 5).

In diseases such as insulin-dependent (type 1) diabetes, non-insulin-dependent (type 2) diabetes and the like, oxidation of lipids is promoted with simultaneous reduction in glucose utilization. This reduction in glucose utilization is one of the factors causing hyperglycemia. When the oxidative glucose metabolism decreases in type 1 and type 2 diabetes and obesity, PDH activity also decreases. It suggests involvement of reduced PDH activity in the reduced glucose utilization in type 1 and type 2 diabetes (e.g., non-patent documents 6, 7).

On the contrary, hepatic gluconeogenesis is enhanced in type 1 and type 2 diabetes, which also forms one factor causing hyperglycemia. The reduced PDH activity increases pyruvic acid concentration, which in turn increases availability of lactic acid as a substrate for hepatic gluconeogenesis. It suggests possible involvement of reduced PDH activity in the enhanced gluconeogenesis in type 1 and type 2 diabetes (e.g., non-patent documents 8, 9). When PDH is activated by inhibition of PDHK, the rate of glucose oxidation is considered to rise. As a result, glucose utilization in the body is promoted and hepatic gluconeogenesis is suppressed, whereby hyperglycemia in type 1 and type 2 diabetes is expected to be improved (e.g., non-patent documents 10, 11, 12). Another factor contributing to diabetes is impaired insulin secretion, which is known to be associated with reduced PDH activity in pancreatic β cells, and introduction of PDHK1, 2 and 4 (e.g., non-patent documents 13, 14). In addition, sustained hyperglycemia due to diabetes is known to cause complications such as diabetic neuropathy, diabetic retinopathy, diabetic nephropathy and the like. Thiamine and α-lipoic acid contribute to activation of PDH as coenzymes. Thiamine and α-lipoic acid, or thiamine derivative and α-lipoic acid derivative are shown to have a promising effect on the treatment of diabetic complications. Thus, activation of PDH is expected to improve diabetic complications (e.g., non-patent documents 15, 16).

Under ischemic conditions, limited oxygen supply reduces oxidation of both glucose and fatty acid and reduces the amount of ATP produced by oxidative phosphorylation in the tissues. In the absence of sufficient oxygen, ATP level is maintained by promoted anaerobic glycolysis. As a result, lactic acid increases and intracellular pH decreases. Even though the body tries to maintain homeostasis of ion by energy consumption, abnormally low ATP level and disrupted cellular osmolarity lead to cell death. In addition, adenosine monophosphate-activating kinase, activated during ischemia, phosphorylates and thus inactivates acetyl-CoA carboxylase. The levels of total malonyl-CoA in the tissue drop, carnitine palmitoyltransferase-I activity is therefore increased and fatty acid oxidation is favored over glucose oxidation by allowing the transport of acyl-CoA into mitochondria. Oxidation of glucose is capable of yielding more ATP per molecule of oxygen than is oxidation of fatty acids. Under ischemic conditions, therefore, when energy metabolism becomes glucose oxidation dominant by activation of PDH, the ability to maintain ATP level is considered to be enhanced (e.g., non-patent document 17).

In addition, since activation of PDH causes oxidation of pyruvic acid produced by glycolysis, and reducing production of lactic acid, the net proton burden is considered to be reduced in ischemic tissues. Accordingly, PDH activation by inhibition of PDHK is expected to protectively act in ischemic diseases such as cardiac muscle ischemia (e.g., non-patent documents 18, 19).

A drug that activates PDH by inhibition of PDHK is considered to decrease lactate production since it promotes pyruvate metabolism. Hence, such drug is expected to be useful for the treatment of hyperlactacidemia such as mitochondrial disease, mitochondrial encephalomyopathy and sepsis (e.g., non-patent document 20).

In cancer cells, the expression of PDHK1 or 2 increases. In cancer cells, moreover, ATP production by oxidative phosphorylation in mitochondria decreases, and ATP production via the anaerobic glycolysis in cytoplasm increases. PDH activation by inhibition of PDHK is expected to promote oxidative phosphorylation in mitochondria, and increase production of active oxygen, which will induce apoptosis of cancer cells. Therefore, the PDH activation by PDHK inhibition is useful for the treatment of cancerous diseases (e.g., non-patent document 21).

Pulmonary hypertension is characterized by high blood pressure caused by partial narrowing of the pulmonary artery due to promoted cell proliferation therein. In pulmonary hypertension, therefore, activation of PDH in the pulmonary artery cell is expected to promote oxidative phosphorylation in mitochondria, increase production of active oxygen, and induce apoptosis of the pulmonary artery cells. Therefore, the PDH activation by PDHK inhibition is considered to be useful for the treatment of pulmonary hypertension (e.g., non-patent document 22).

Energy production and glucose metabolism in the cerebrum decrease in Alzheimer disease, and also, PDH activity declines. When the PDH activity declines, production of acetyl CoA decreases. Acetyl CoA is utilized for ATP production in the electron transport system via the citric acid cycle. Acetyl CoA is also a starting material for synthesizing acetylcholine, which is one of the neurotransmitters. Therefore, reduced brain PDH activity in Alzheimer disease is considered to cause neuronal cell death due to the decreased ATP production. Moreover, it is considered that synthesis of acetylcholine, which is the transmitter for cholinergic nerve, is inhibited to induce deterioration of memory and the like. Activation of PDH in the brain is expected to enhance energy production and acetylcholine synthesis in Alzheimer disease. Therefore, activation of PDH by the inhibition of PDHK is considered to be useful for the treatment of Alzheimer disease (e.g., non-patent documents 23, 24).

It has been shown that dichloroacetic acid, which is a drug having a PDH activating action, provides promising effects for the treatment of diabetes, myocardial ischemia, myocardial infarction, angina pectoris, cardiac failure, hyperlactacidemia, brain ischemia, cerebral apoplexy, peripheral arterial disease, chronic obstructive pulmonary disease, cancerous disease, and pulmonary hypertension (e.g., non-patent documents 10, 18, 20, 22, 25, 26, 27).

From the foregoing findings, a PDHK inhibitor is considered to be useful for the prophylaxis or treatment of diseases relating to glucose utilization disorder, for example, diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.). Furthermore, a PDHK inhibitor is considered to be useful for the prophylaxis or treatment of diseases caused by limited energy substrate supply to the tissues, for example, cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia and cerebral apoplexy.

Therefore, a PDHK inhibitor is considered to be useful for the treatment or prophylaxis of diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease.

DOCUMENT LIST

Non-Patent Documents non-patent document 1: Reed L J, Hackert M L. Structure-function relationships in dihydrolipoamide acyltransferases. J Biol. Chem. 1990 Jun. 5; 265(16):8971-4.

non-patent document 2: Patel M S, Roche T E. Molecular biology and biochemistry of pyruvate dehydrogenase complexes. FASEB J. 1990 November; 4(14):3224-33.

non-patent document 3: Sugden M C, Holness M J. Recent advances in mechanisms regulating glucose oxidation at the level of the pyruvate dehydrogenase complex by PDK5. Am J Physiol Endocrinol Metab. 2003 May; 284(5):E855-62.

non-patent document 4: Bowker-Kinley M M, Davis W I, Wu P, Harris R A, Popov K M. Evidence for existence of tissue-specific regulation of the mammalian pyruvate dehydrogenase complex. Biochem J. 1998 Jan. 1; 329 (Pt 1):191-6.

non-patent document 5: Kim J W, Tchernyshyov I, Semenza G L, Dang C V. HIF-1-mediated expression of pyruvate dehydrogenase kinase: a metabolic switch required for cellular adaptation to hypoxia. Cell Metab. 2006 March; 3(3):177-85.

non-patent document 6: Morino K, Petersen K F, Dufour S, Befroy D, Frattini J, Shatzkes N, et al. Reduced mitochondrial density and increased IRS-1 serine phosphorylation in muscle of insulin-resistant offspring of type 2 diabetic parents. J Clin Invest. 2005 December; 115(12):3587-93.

non-patent document 7: Caterson I D, Fuller S J, Randle P J. Effect of the fatty acid oxidation inhibitor 2-tetradecylglycidic acid on pyruvate dehydrogenase complex activity in starved and alloxan-diabetic rats. Biochem J. 1982 Oct. 15; 208(1):53-60.

non-patent document 8: Boden G, Chen X, Stein T P. Gluconeogenesis in moderately and severely hyperglycemic patients with type 2 diabetes mellitus. Am J Physiol Endocrinol Metab. 2001 January; 280(1):E23-30.

non-patent document 9: Shangraw R E, Fisher D M. Pharmacokinetics and pharmacodynamics of dichloroacetate in patients with cirrhosis. Clin Pharmacol Ther. 1999 October; 66(4):380-90.

non-patent document 10: Stacpoole P W, Moore G W, Kornhauser D M. Metabolic effects of dichloroacetate in patients with diabetes mellitus and hyperlipoproteinemia. N Engl J. Med. 1978 Mar. 9; 298(10):526-30.

non-patent document 11: Mayers R M, Leighton B, Kilgour E. PDH kinase inhibitors: a novel therapy for Type II diabetes? Biochem Soc Trans. 2005 April; 33(Pt 2):367-70.

non-patent document 12: Jeoung N H, Rahimi Y, Wu P, Lee W N, Harris R A. Fasting induces ketoacidosis and hypothermia in PDHK2/PDHK4-double-knockout mice. Biochem J. 2012 May 1; 443(3):829-39.

non-patent document 13: Zhou Y P, Berggren P O, Grill V. A fatty acid-induced decrease in pyruvate dehydrogenase activity is an important determinant of beta-cell dysfunction in the obese diabetic db/db mouse. Diabetes. 1996 May; 45(5):580-6.

non-patent document 14: Xu J, Han J, Epstein P N, Liu Y Q. Regulation of PDK mRNA by high fatty acid and glucose in pancreatic islets. Biochem Biophys Res Commun. 2006 Jun. 9; 344(3):827-33.

non-patent document 15: Benfotiamine. Monograph. Altern Med Rev. 2006 September; 11(3):238-42.

non-patent document 16: Vallianou N, Evangelopoulos A, Koutalas P. Alpha-lipoic Acid and diabetic neuropathy. Rev Diabet Stud. 2009 Winter; 6(4):230-6.

non-patent document 17: Ussher J R, Lopaschuk G D. The malonyl CoA axis as a potential target for treating ischaemic heart disease. Cardiovasc Res. 2008 Jul. 15; 79(2):259-68.

non-patent document 18: Wargovich T J, MacDonald R G, Hill J A, Feldman R L, Stacpoole P W, Pepine C J. Myocardial metabolic and hemodynamic effects of dichloroacetate in coronary artery disease. Am J. Cardiol. 1988 Jan. 1; 61(1):65-70.

non-patent document 19: Taniguchi M, Wilson C, Hunter C A, Pehowich D J, Clanachan A S, Lopaschuk G D. Dichloroacetate improves cardiac efficiency after ischemia independent of changes in mitochondrial proton leak. Am J Physiol Heart Circ Physiol. 2001 April; 280(4):H1762-9.

non-patent document 20: Stacpoole P W, Nagaraja N V, Hutson A D. Efficacy of dichloroacetate as a lactate-lowering drug. J Clin Pharmacol. 2003 July; 43(7):683-91.

non-patent document 21: Bonnet S, Archer S L, Allalunis-Turner J, Haromy A, Beaulieu C, Thompson R, et al. A mitochondria-K+ channel axis is suppressed in cancer and its normalization promotes apoptosis and inhibits cancer growth. Cancer Cell. 2007 January; 11(1):37-51.

non-patent document 22: McMurtry M S, Bonnet S, Wu X, Dyck J R, Haromy A, Hashimoto K, et al. Dichloroacetate prevents and reverses pulmonary hypertension by inducing pulmonary artery smooth muscle cell apoptosis. Circ Res. 2004 Oct. 15; 95(8):830-40.

non-patent document 23: Saxena U. Bioenergetics breakdown in Alzheimer's disease: targets for new therapies. Int J Physiol Pathophysiol Pharmacol. 2011; 3(2):133-9.

non-patent document 24: Stacpoole P W. The pyruvate dehydrogenase complex as a therapeutic target for age-related diseases. Aging Cell. 2012 June; 11(3):371-7.

non-patent document 25: Marangos P J, Turkel C C, Dziewanowska Z E, Fox A W. Dichloroacetate and cerebral ischaemia therapeutics. Expert Opin Investig Drugs. 1999 April; 8(4):373-82.

non-patent document 26: Calvert L D, Shelley R, Singh S J, Greenhaff P L, Bankart J, Morgan M D, et al. Dichloroacetate enhances performance and reduces blood lactate during maximal cycle exercise in chronic obstructive pulmonary disease. Am J Respir Crit. Care Med. 2008 May 15; 177(10):1090-4.

non-patent document 27: Flavin D F. Non-Hodgkin's Lymphoma Reversal with Dichloroacetate. J. Oncol. Hindawi Publishing Corporation Journal of Oncology, Volume 2010, Article ID 414726, 4 pages doi:10.1155/2010/414726.

SUMMARY OF THE INVENTION

The present invention is as follow.

[1] A compound represented by the formula [I]:

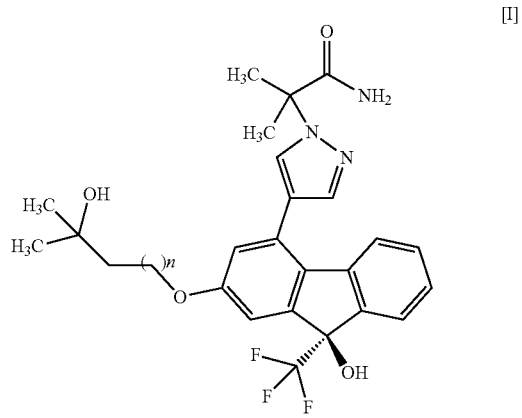

wherein n is 1 or 2,
or a pharmaceutically acceptable salt thereof,

[2] a compound represented by the formula:

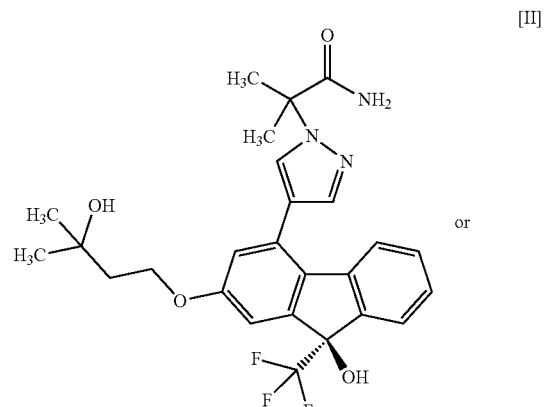

or

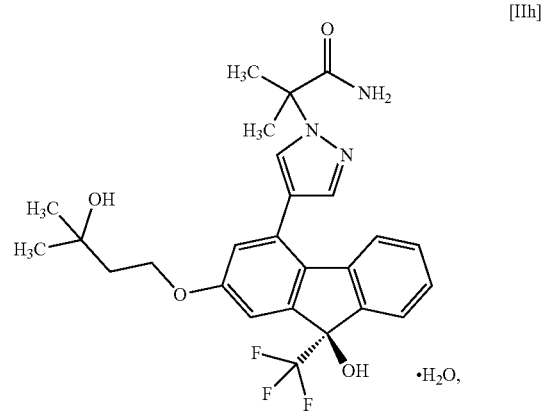

[3] the compound of the above-mentioned [2], which is represented by the formula [II]:

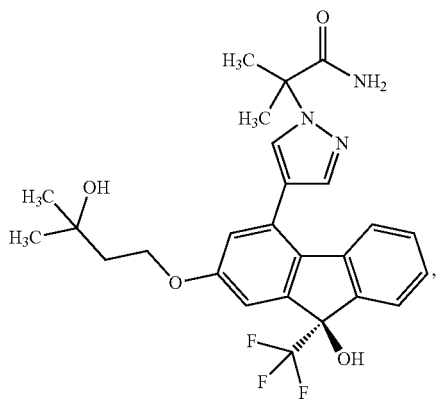

[4] the compound of the above-mentioned [2], which is represented by the formula [IIh]:

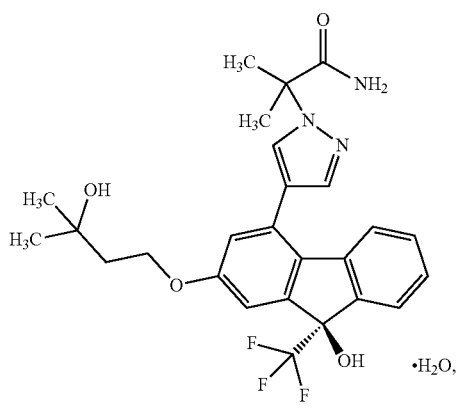

[5] a compound represented by the formula [III]:

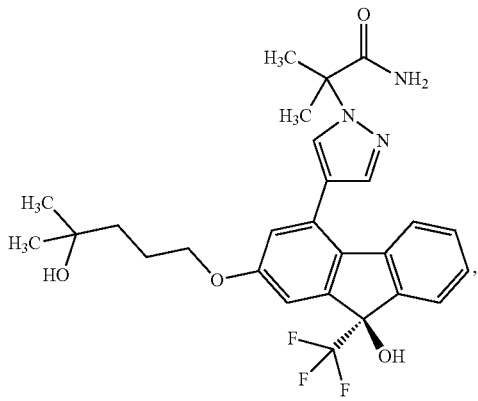

[6] a pharmaceutical composition comprising the compound of any of the above-mentioned [1] to [5], or a pharmaceutically acceptable salt thereof, and a pharmaceutically acceptable carrier,

[7] a PDHK inhibitor comprising the compound of any of the above-mentioned [1] to [5], or a pharmaceutically acceptable salt thereof,

[8] a PDHK1 inhibitor comprising the compound of any of the above-mentioned [1] to [5], or a pharmaceutically acceptable salt thereof,

[9] a PDHK2 inhibitor comprising the compound of any of the above-mentioned [1] to [5], or a pharmaceutically acceptable salt thereof,

[10] a hypoglycemic agent comprising the compound of any of the above-mentioned [1] to [5], or a pharmaceutically acceptable salt thereof,

[11] a lactic acid-lowering agent comprising the compound of any of the above-mentioned [1] to [5], or a pharmaceutically acceptable salt thereof,

[12] an agent for the prophylaxis or treatment of diabetes, insulin resistance syndrome, metabolic syndrome, hyperglycemia, hyperlactacidemia, diabetic complications, cardiac failure, cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer or pulmonary hypertension, which comprises the compound of any of the above-mentioned [1] to [5], or a pharmaceutically acceptable salt thereof,

[12'] an agent for the prophylaxis or treatment of diabetes, insulin resistance syndrome, metabolic syndrome, hyperglycemia, hyperlactacidemia, diabetic complications, cardiac failure, cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease, which comprises the compound of any of the above-mentioned [1] to [5], or a pharmaceutically acceptable salt thereof,

[13] the prophylactic or therapeutic agent of the above-mentioned [12], wherein the diabetes is type 1 diabetes or type 2 diabetes,

[14] the prophylactic or therapeutic agent of the above-mentioned [12], wherein the diabetic complications are selected from the group consisting of diabetic neuropathy, diabetic retinopathy, diabetic nephropathy and cataract,

[15] the prophylactic or therapeutic agent of the above-mentioned [12], wherein the cardiac failure is acute cardiac failure or chronic cardiac failure,

[16] a pharmaceutical composition comprising
(a) the compound of any of the above-mentioned [1] to [5], or a pharmaceutically acceptable salt thereof, and
(b) at least one other medicament effective for the prophylaxis or treatment of a disease selected from the group consisting of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension,

[16'] a pharmaceutical composition comprising
(a) the compound of any of the above-mentioned [1] to [5], or a pharmaceutically acceptable salt thereof, and
(b) at least one other medicament effective for the prophylaxis or treatment of a disease selected from the group consisting of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer, pulmonary hypertension and Alzheimer disease,

[17] a combination drug comprising
(a) the compound of any of the above-mentioned [1] to [5], or a pharmaceutically acceptable salt thereof, and
(b) at least one other medicament effective for the prophylaxis or treatment of a disease selected from the group consisting of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer and pulmonary hypertension, which are administered simultaneously, separately or continuously.

[17'] a combination drug comprising
(a) the compound of any of the above-mentioned [1] to [5], or a pharmaceutically acceptable salt thereof, and
(b) at least one other medicament effective for the prophylaxis or treatment of a disease selected from the group consisting of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension and Alzheimer disease, which are administered simultaneously, separately or continuously.

[18] a method of inhibiting PDHK in a mammal, comprising administering a pharmaceutically effective amount of the compound of any of the above-mentioned [1] to [5], or a pharmaceutically acceptable salt thereof to said mammal,

[19] a method of inhibiting PDHK1 in a mammal, comprising administering a pharmaceutically effective amount of the compound of any of the above-mentioned [1] to [5], or a pharmaceutically acceptable salt thereof to said mammal,

[20] a method of inhibiting PDHK2 in a mammal, comprising administering a pharmaceutically effective amount of the compound of any of the above-mentioned [1] to [5], or a pharmaceutically acceptable salt thereof to said mammal,

[21] a method for the prophylaxis or treatment of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer or pulmonary hypertension in a mammal, comprising administering a pharmaceutically effective amount of the compound of any of the above-mentioned [1] to [5], or a pharmaceutically acceptable salt thereof to said mammal,

[21'] a method for the prophylaxis or treatment of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease in a mammal, comprising administering a pharmaceutically effective amount of the compound of any of the above-mentioned [1] to [5], or a pharmaceutically acceptable salt thereof to said mammal,

[22] a method of decreasing the blood glucose level in a mammal, comprising administering a pharmaceutically effective amount of the compound of any of the above-mentioned [1] to [5], or a pharmaceutically acceptable salt thereof to said mammal,

[23] a method of decreasing the lactate level in a mammal, comprising administering a pharmaceutically effective amount of the compound of any of the above-mentioned [1] to [5], or a pharmaceutically acceptable salt thereof to said mammal,

[24] use of the compound of any of the above-mentioned [1] to [5], or a pharmaceutically acceptable salt thereof for the production of a PDHK inhibitor,

[25] use of the compound of any of the above-mentioned [1] to [5], or a pharmaceutically acceptable salt thereof for the production of a PDHK1 inhibitor,

[26] use of the compound of any of the above-mentioned [1] to [5], or a pharmaceutically acceptable salt thereof for the production of a PDHK2 inhibitor,

[27] use of the compound of any of the above-mentioned [1] to [5], or a pharmaceutically acceptable salt thereof for the production of a blood glucose level-lowering agent,

[28] use of the compound of any of the above-mentioned [1] to [5], or a pharmaceutically acceptable salt thereof for the production of a lactate level-lowering agent,

[29] use of the compound of any of the above-mentioned [1] to [5], or a pharmaceutically acceptable salt thereof for the production of a prophylactic or therapeutic agent for diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer or pulmonary hypertension,

[29'] use of the compound of any of the above-mentioned [1] to [5], or a pharmaceutically acceptable salt thereof for the production of a prophylactic or therapeutic agent for diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease,

[30] the use of any of the above-mentioned [24] to [29], in combination with at least one other medicament effective for the prophylaxis or treatment of a disease selected from the group consisting of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer and pulmonary hypertension, and

[30'] the use of any of the above-mentioned [24] to [29], in combination with at least one other medicament effective for the prophylaxis or treatment of a disease selected from the group consisting of diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension and Alzheimer disease, and the like.

EFFECT OF THE INVENTION

The compound of the present invention or a pharmaceutically acceptable salt thereof inhibits a PDHK activity, and is useful as a therapeutic or prophylactic agent for diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease, and the like.

DESCRIPTION OF EMBODIMENTS

Figure 1:
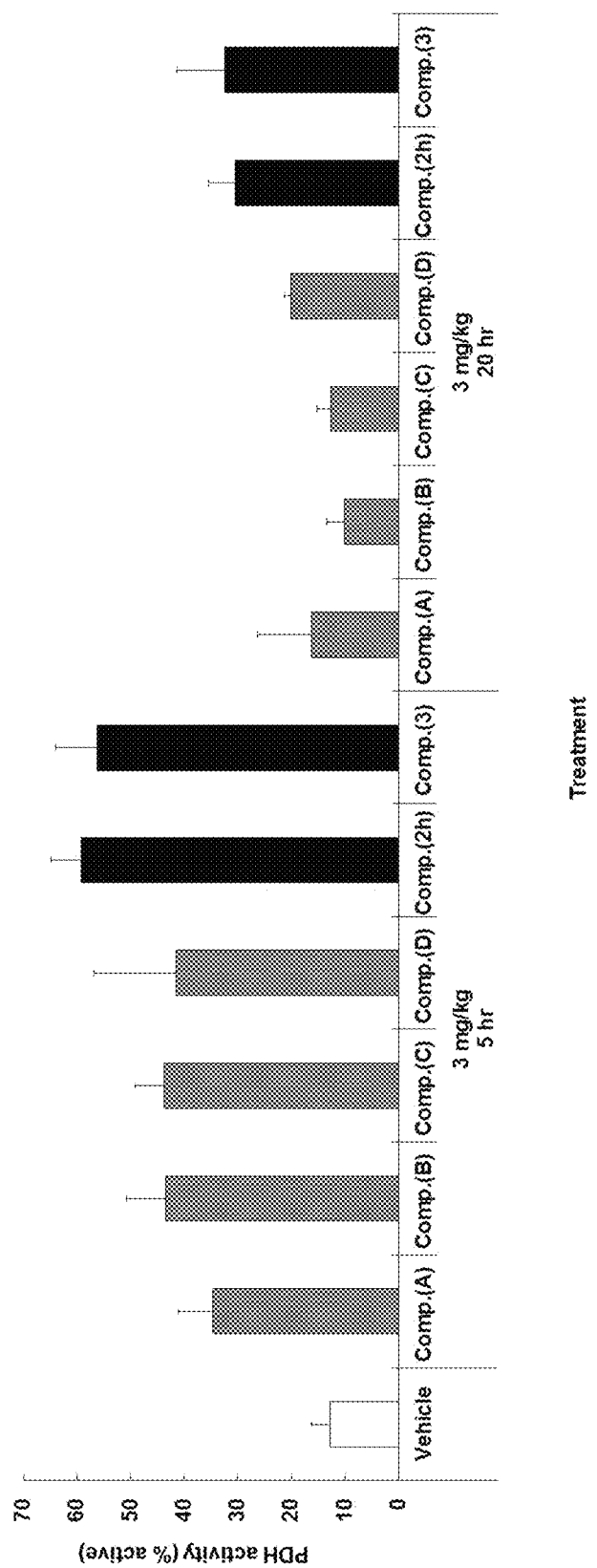
FIG. 1 shows an effect of test compounds on the liver PDH activity (percentage of active liver PDH activity to the total liver PDH activity) in non-fasting SD(IGS) rats (mean±standard deviation (n=3)).

The present invention is explained in detail in the following.

The compound of the present invention is a compound represented by the formula [I]:

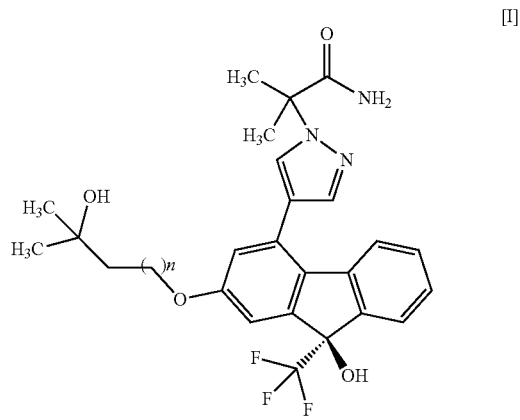

wherein n is 1 or 2, (hereinafter to be also referred to as compound (1)), or a pharmaceutically acceptable salt thereof.

The compound of the present invention is a compound represented by the formula [II]:

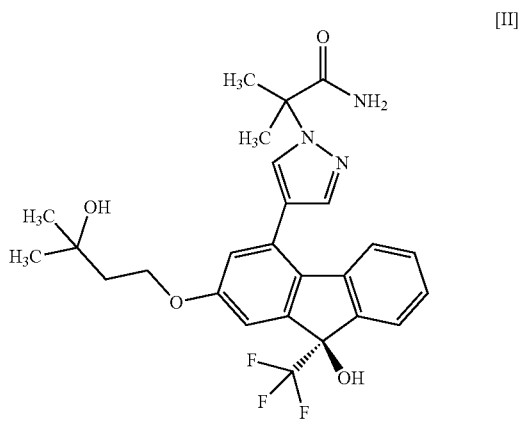 [SMILES: CC(C)(O)CCOc1cc(-c2cnn(C(C)(C)C(N)=O)c2)c2c(c1)[C@@](O)(C(F)(F)F)c1ccccc1-2]

(2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamide) (hereinafter to be also referred to as compound (2)).

The compound of the present invention is a compound represented by the formula [IIh]:

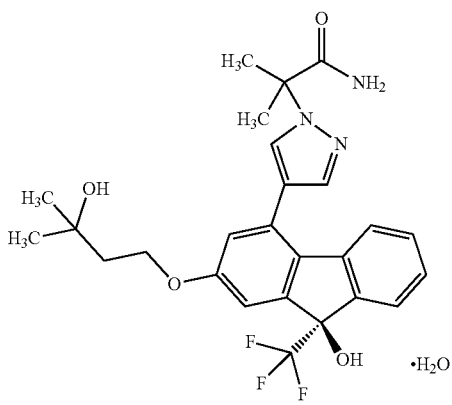

(2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamide monohydrate) (hereinafter to be also referred to as compound (2h)).

The compound of the present invention is a compound represented by the formula [III]:

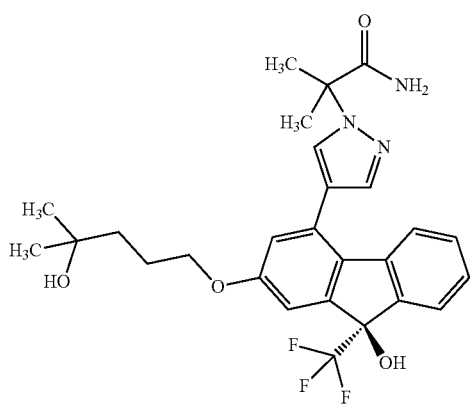

(2-{4-[(9R)-9-hydroxy-2-(4-hydroxy-4-methylpentyloxy)-9-(trifluoromethyl)-9H-fluoren-4-yl]-1H-pyrazol-1-yl}-2-methylpropanamide) (hereinafter to be also referred to as compound (3)).

A pharmaceutically acceptable salt of the compound of the present invention may be any salt as long as it forms a non-toxic salt with the compound of the present invention. Examples thereof include salts with inorganic acids, salts with organic acids, salts with amino acids and the like.

Examples of the salt with inorganic acid include a salt with hydrochloric acid, nitric acid, sulfuric acid, phosphoric acid, hydrobromic acid and the like.

Examples of the salt with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with amino acid include salts with lysine, arginine, aspartic acid, glutamic acid and the like.

A pharmaceutically acceptable salt of the compound of the present invention is preferably a salt with an inorganic acid.

In addition, the compound of the present invention or a pharmaceutically acceptable salt thereof may be labeled with an isotope (e.g., $^3H$, $^{14}C$, $^{35}S$ etc.).

As the compound of the present invention or a pharmaceutically acceptable salt thereof, compound (1) or a pharmaceutically acceptable salt thereof, each of which is substantially purified, is preferable. More preferred is the compound of the present invention or a pharmaceutically acceptable salt thereof, each of which is purified to a purity of not less than 80%.

The compound of the formula [I] or a pharmaceutically acceptable salt thereof may exist as a solvate. The term "solvate" refers to the compound of the formula [I] or a pharmaceutically acceptable salt thereof with which a solvent molecule is associated, and also includes hydrates. Such solvates are preferably pharmaceutically acceptable solvates. Such solvates include, for example, hydrate, ethanol solvate, dimethylsulfoxide-solvate and the like of the compound of the formula [I] or a pharmaceutically acceptable salt thereof. Specific examples include hemihydrate, monohydrate, dihydrate or mono(ethanol)solvate of the compound of the formula [I] or a monohydrate of the compound of the formula [I], 2/3(ethanol)solvate of dihydrochloride of the same and the like. Such solvates can be produced according to conventional methods.

Examples of the "pharmaceutical composition" include oral preparations such as tablet, capsule, granule, powder, troche, syrup, emulsion, suspension and the like, and parenteral agents such as external preparation, suppository, injection, eye drop, nasal preparation, pulmonary preparation and the like.

The pharmaceutical composition of the present invention is produced according to a method known per se in the art of pharmaceutical preparations, by mixing the compound of the present invention or a pharmaceutically acceptable salt thereof with a suitable amount of at least one kind of pharmaceutically acceptable carrier and the like as appropriate. While the content of the compound of the present invention or a pharmaceutically acceptable salt thereof in the pharmaceutical composition varies depending on the dosage form, dose and the like, it is, for example, 0.1 to 100 wt % of the whole composition.

Examples of the "pharmaceutically acceptable carrier" include various organic or inorganic carrier substances conventionally used as preparation materials, for example, excipient, disintegrant, binder, fluidizer, lubricant and the like for solid preparations, and solvent, solubilizing agent, suspending agent, isotonicity agent, buffering agent, soothing agent and the like for liquid preparations. Where necessary, moreover, additives such as preservative, antioxidant, colorant, sweetening agent and the like are used.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "fluidizer" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agents" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonic agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color yellow No. 4 or 5 etc.), β-carotene and the like.

Examples of the "sweetening agent" include saccharin sodium, dipotassium glycyrrhizinate, aspartame and the like.

The pharmaceutical composition of the present invention can be administered orally or parenterally (e.g., topical, intramuscular, subcutaneous, rectal, intravenous administration etc.) to human as well as mammals other than human (e.g., mouse, rat, hamster, guinea pig, rabbit, cat, dog, swine, bovine, horse, sheep, monkey etc.). The dose varies depending on the subject of administration, disease, symptom, dosage form, administration route and the like. For example, the daily dose for oral administration to an adult patient (body weight: about 60 kg) is generally within the range of about 1 mg to 1 g, based on compound (1) as the active ingredient. This amount can be administered in one to several portions.

Since the compound of the present invention or a pharmaceutically acceptable salt thereof has a PDHK (PDHK1 and/or PDHK2) inhibitory activity, it is considered to be advantageous for the treatment or prophylaxis of the diseases relating to an impairment of glucose utilization, for example, diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.). In addition, the PDHK inhibitor is considered to be advantageous for the treatment or prophylaxis of diseases wherein supply of an energy substrate to a tissue is limited, for example, cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia and cerebral apoplexy. Furthermore, the PDHK inhibitor is considered to be advantageous for the treatment or prophylaxis of a mitochondrial disease, mitochondrial encephalomyopathy, cancer pulmonary hypertension or Alzheimer disease, and the like.

Diabetes is, for example, type 1 diabetes or type 2 diabetes.

Examples of the diabetic complications include diabetic neuropathy, diabetic retinopathy, diabetic nephropathy and cataract.

Cardiac failure is, for example, acute cardiac failure or chronic cardiac failure.

To "inhibit PDHK" means to inhibit the function of PDHK and eliminate or attenuate the activity. To "inhibit PDHK", human PDHK is preferably inhibited. As a "PDHK inhibitor", preferred is a "human PDHK inhibitor".

To "inhibit PDHK1" means to inhibit the function of PDHK1 and eliminate or attenuate the activity. For example, it means to inhibit the function as PDHK1 based on the conditions in the below-mentioned Experimental Example 1. To "inhibit PDHK1", human PDHK1 is preferably inhibited. As a "PDHK1 inhibitor", preferred is a "human PDHK1 inhibitor". More preferred is a "PDHK1 inhibitor for human target organ".

To "inhibit PDHK2" means to inhibit the function of PDHK2 and eliminate or attenuate the activity. For example, it means to inhibit the function as PDHK2 based on the conditions in the below-mentioned Experimental Example 1. To "inhibit PDHK2", human PDHK2 is preferably inhibited. As a "PDHK2 inhibitor", preferred is a "human PDHK2 inhibitor". More preferred is a "PDHK2 inhibitor for human target organ".

To "activate PDH" means to activate PDH in a target organ (e.g., liver, skeletal muscle, adipose tissue, heart, brain) and the like, cancer or the like.

To "decrease blood glucose level" means to decrease the glucose concentration in blood (including in serum and plasma), preferably to decrease high blood glucose level, more preferably, to decrease the blood glucose level to a therapeutically effective normal level for human.

To "decrease lactic acid level" means to decrease the lactic acid concentration in blood (including in serum and plasma), preferably to decrease high lactic acid level, more preferably, to decrease the lactic acid level to a therapeutically effective normal level for human.

The compound of the present invention or a pharmaceutically acceptable salt thereof can be used in combination with one or a plurality of other medicaments (hereinafter to be also referred to as a concomitant drug) according to a method generally employed in the medical field (hereinafter to be referred to as combined use).

The administration period of the compound of the present invention or a pharmaceutically acceptable salt thereof, and a concomitant drug is not limited, and they may be administered to an administration subject as combination preparation, or the both preparations may be administered simultaneously or at given intervals. In addition, the pharmaceutical composition of the present invention and a concomitant drug may be used as a medicament in the form of a kit. The dose of the concomitant drug is similar to the clinically-employed dose and can be appropriately selected according to the subject of administration, disease, symptom, dosage form, administration route, administration time, combination and the like. The administration form of the concomitant drug is not particularly limited, and it only needs to be combined with the compound of the present invention or a pharmaceutically acceptable salt thereof.

Examples of the combination drug include therapeutic agents and/or prophylaxis agents for diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease, and the like, and one or more agents therefrom and the compound of the present invention or a pharmaceutically acceptable salt thereof can be used in combination.

Examples of the "agent for the treatment and/or prophylaxis of diabetes" include insulin preparation, sulfonylurea hypoglycemic agent, metformin, DPP-4 inhibitor, insulin resistance improving agent (for example, thiazolidine derivative), GLP-1 receptor agonist and the like.

EXAMPLES

The production method of the compound of the present invention or a pharmaceutically acceptable salt thereof is specifically explained by Examples. However, the present invention is not limited by these Examples.

Even if no description is found in the present production method, steps may be modified for efficient production, such as introduction of a protecting group into a functional group where necessary with deprotection in a subsequent step, using a functional group as a precursor in each step, followed by conversion to a desired functional group at a suitable stage, changing the order of production methods and steps, and the like.

The treatment after reaction in each step may be performed by a conventional method, where isolation and purification can be performed as necessary according to a method appropriately selected from conventional methods such as crystallization, recrystallization, distillation, partitioning, silica gel chromatography, preparative HPLC and the like, or a combination thereof. All reagents and solvents have quality of commercially available products, and were used without purification.

Percentage % shows wt %. Other abbreviations used in the example section mean the following.
s: singlet
d: doublet
t: triplet
q: quartet
m: multiplet
br: broad
dd: double doublet
td: triple doublet
ddd: double double doublet
J: coupling constant
$CDCl_3$: deuterated chloroform
DMSO-$D_6$: deuterated dimethyl sulfoxide
$^1$H NMR: proton nuclear magnetic resonance
HPLC: high performance liquid chromatography
DPPA: diphenylphosphoryl azide
$^1$H-NMR spectrum was measured in $CDCl_3$ or DMSO-$D_6$ using tetramethylsilane as an internal standard, and all δ values are shown in ppm.
(10 mM Phosphate Buffer (pH 2.0))

Sodium dihydrogen phosphate (3.60 g) was dissolved in water (3000 ml), and adjusted to pH 2.0 with phosphoric acid to give the title buffer.
HPLC Analysis Conditions
Analysis Condition 1
Measurement device: HPLC system SHIMADZU CORPORATION high-performance liquid chromatograph Prominence
Column: DAICEL CHIRALCEL OD-3R 4.6 mmΦ×150 mm
Column temperature: 40° C.
Mobile phase: (SOLUTION A) 10 mM phosphate buffer (pH 2.0), (SOLUTION B) acetonitrile The composition of the mobile phase (SOLUTION A:SOLUTION B) was linearly changed from 50:50 to 20:80 over 20 min and then maintained at 20:80 for 5 min.
Flow rate: 0.5 ml/min
Detection: UV (220 nm)
Analysis Condition 2
Measurement device: HPLC system SHIMADZU CORPORATION high-performance liquid chromatograph Prominence
Column: DAICEL CHIRALCEL OJ-RH 4.6 mmΦ×150 mm
Column temperature: 40° C.
Mobile phase: (SOLUTION A) 10 mM phosphate buffer (pH 2.0), (SOLUTION B) acetonitrile The composition of the mobile phase (SOLUTION A:SOLUTION B) was linearly changed from 70:30 to 40:60 over 20 min and then maintained at 40:60 for 10 min.
Flow rate: 0.5 ml/min
Detection: UV (220 nm)
Analysis Condition 3
Measurement device: HPLC system SHIMADZU CORPORATION high-performance liquid chromatograph Prominence
Column: DAICEL CHIRALPAK AD-3R 4.6 mmΦ×150 mm
Column temperature: 40° C.
Mobile phase: (SOLUTION A) 10 mM phosphate buffer (pH 2.0), (SOLUTION B) acetonitrile The composition of the mobile phase (SOLUTION A:SOLUTION B) was linearly changed from 50:50 to 20:80 over 20 min and then maintained at 20:80 for 5 min.
Flow rate: 0.5 ml/min
Detection: UV (220 nm)

Example 1

Synthesis of 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamide (compound (2))

Step 1

Ethyl 2'-chloro-4'-methoxybiphenyl-2-carboxylate

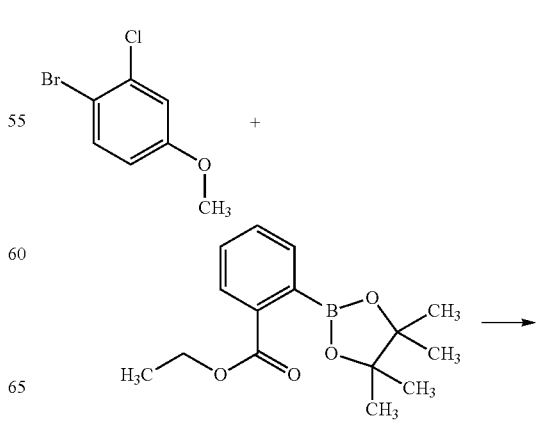

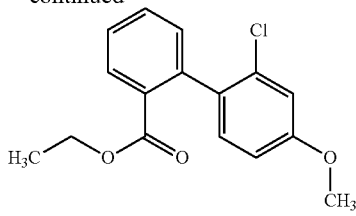

Under an argon atmosphere, 1-bromo-2-chloro-4-methoxybenzene (44.3 g) was dissolved in toluene (220 ml), ethyl 2-(4,4,5,5-tetramethyl[1,3,2]dioxaborolan-2-yl)benzoate (60.8 g), water (132 ml), sodium hydrogen carbonate (33.6 g) and dichlorobis(triphenylphosphine)palladium(II) (2.8 g) were added, and the mixture was stirred at an oil bath temperature of 120° C. for 7 hr. To the reaction mixture was added ethyl 2-(4,4,5,5-tetramethyl[1,3,2]dioxaborolan-2-yl)benzoate (5.2 g), and the mixture was further stirred for 2 hr. The reaction mixture was cooled to room temperature, toluene (100 ml) and water (200 ml) were added, and the mixture was stirred overnight. To the reaction mixture was added activated carbon (3 g), and the mixture was further stirred for 1 hr. The insoluble material was filtered off through celite, and the insoluble material was washed with toluene (100 ml) and water (200 ml). The obtained filtrates were combined to allow for layer separation. The obtained organic layer was washed with water (100 ml), and the solvent was evaporated to give the title compound (67.7 g).

$^1$H-NMR (400 MHz, DMSO-D$_6$) δ: 7.88-7.86 (1H, m), 7.63 (1H, td, J=7.6, 1.4 Hz), 7.51 (1H, td, J=7.6, 1.4 Hz), 7.27 (1H, dd, J=7.6, 0.9 Hz), 7.18 (1H, d, J=8.6 Hz), 7.06 (1H, d, J=2.6 Hz), 6.95 (1H, dd, J=8.6, 2.6 Hz), 4.01 (2H, m), 3.80 (3H, s), 0.96 (3H, t, J=7.1 Hz).

Step 2

2'-Chloro-4'-methoxybiphenyl-2-carboxylic acid

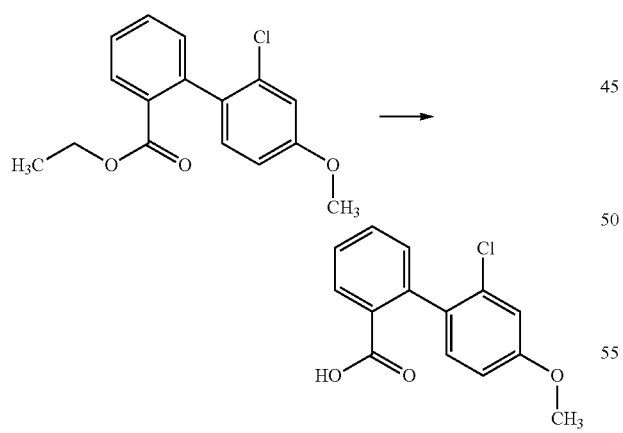

Ethyl 2'-chloro-4'-methoxybiphenyl-2-carboxylate (67.7 g) was dissolved in ethanol (100 ml), 4N aqueous sodium hydroxide (100 ml) was added, and the mixture was stirred at an oil bath temperature of 110° C. for 4.5 hr. The reaction mixture was cooled to room temperature, water (200 ml) and toluene (100 ml) were added, and the mixture was stirred overnight. To the reaction mixture was added activated carbon (3.6 g), and the mixture was further stirred for 1 hr. The insoluble material was filtered off through celite, and the insoluble material was washed with toluene (30 ml) and water (300 ml). The obtained filtrates were combined to allow for layer separation. The obtained aqueous layer was washed with toluene (100 ml), the aqueous layer was acidified with concentrated hydrochloric acid (40 ml), and stirred at room temperature for 1 hr. The precipitated solid was collected by filtration. The obtained solid was air-dried for 3 hr, and dried under reduced pressure at 60° C. overnight to give the title compound (50.2 g).

$^1$H-NMR (400 MHz, DMSO-D$_6$) δ: 12.57 (1H, s), 7.90-7.88 (1H, m), 7.60 (1H, td, J=7.6, 1.3 Hz), 7.49 (1H, td, J=7.6, 1.3 Hz), 7.24 (1H, dd, J=7.6, 1.0 Hz), 7.19 (1H, d, J=8.4 Hz), 7.06 (1H, d, J=2.4 Hz), 6.95 (1H, dd, J=8.5, 2.4 Hz), 3.81 (3H, s).

Step 3

4-Chloro-2-methoxy-9H-fluoren-9-one

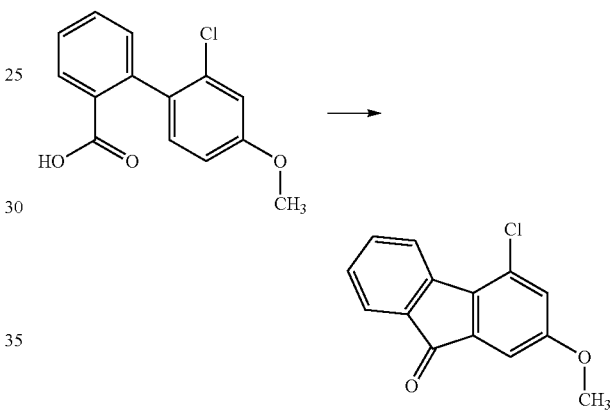

Under an argon atmosphere, to 2'-chloro-4'-methoxybiphenyl-2-carboxylic acid (65.4 g) was added an Eaton reagent (phosphorus pentoxide-methanesulfonic acid (weight ratio 1:10) solution, 330 ml), and the mixture was stirred at an oil bath temperature of 100° C. for 1 hr. The reaction mixture was ice-cooled, water (650 ml) was slowly added dropwise, and the mixture was stirred at room temperature for 1 hr. The precipitated solid was collected by filtration, and washed with water (500 ml). The obtained solid was air-dried overnight to give the title compound (92.0 g).

$^1$H-NMR (400 MHz, DMSO-D$_6$) δ: 8.01 (1H, d, J=7.4 Hz), 7.64-7.60 (2H, m), 7.36 (1H, td, J=7.4, 0.9 Hz), 7.17 (2H, dd, J=8.4, 2.3 Hz), 3.85 (3H, s).

Step 4

4-Chloro-2-hydroxy-9H-fluoren-9-one

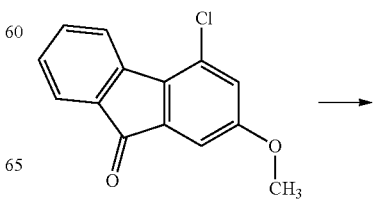

-continued

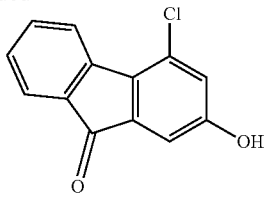

Under an argon atmosphere, to 4-chloro-2-methoxy-9H-fluoren-9-one (92.0 g) were added N-methylpyrrolidone (120 ml) and pyridine hydrochloride (144 g). The reaction mixture was stirred at an oil bath temperature of 200° C. for 3 hr with removing water by a Dean-Stark apparatus. The reaction mixture was cooled to 90° C., water (600 ml) was added dropwise, and the mixture was stirred at room temperature for 2 hr. The precipitated solid was collected by filtration, and washed with water (400 ml). The obtained solid was air-dried for 3 days, a mixed solvent of hexane and ethyl acetate (hexane:ethyl acetate 1:1, 300 ml) was added, and the mixture was stirred at room temperature for 1 hr. The solid was collected by filtration, and washed with a mixed solvent of hexane and ethyl acetate (hexane:ethyl acetate=1:1, 500 ml). The obtained solid was dried under reduced pressure at 50° C. for 3 hr to give the title compound (48.6 g).

$^1$H-NMR (400 MHz, DMSO-$D_6$) δ: 10.56 (1H, s), 7.96 (1H, d, J=8.4 Hz), 7.61-7.57 (2H, m), 7.32 (1H, td, J=7.4, 0.9 Hz), 6.97 (1H, d, J=2.2 Hz), 6.94 (1H, d, J=2.2 Hz).

Step 5

Ethyl 4-(4-chloro-9-oxo-9H-fluoren-2-yloxy)butyrate

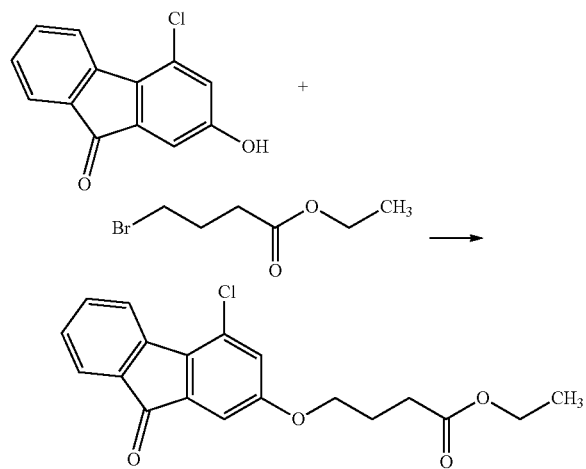

4-Chloro-2-hydroxy-9H-fluoren-9-one (48.6 g) was dissolved in N,N-dimethylformamide (150 ml), potassium carbonate (58.3 g) and ethyl 4-bromobutyrate (33.5 ml) were added, and the mixture was stirred at 60° C. for 2 hr. The reaction mixture was cooled to 40° C., and toluene (300 ml) and water (300 ml) were added to allow for layer separation. The obtained aqueous layer was extracted again with toluene (100 ml). The obtained organic layers were combined, washed twice with water (100 ml), anhydrous sodium sulfate and activated carbon (2.5 g) were added, and the mixture was stirred at room temperature for 5 min. The insoluble material was filtered off through celite, and the solvent in the filtrate was evaporated. To the obtained residue was added hexane (220 ml), and the mixture was stirred at 50° C. for 10 min and at room temperature for 1 hr. The precipitated solid was collected by filtration, and washed with hexane. The obtained solid was dried under reduced pressure to give the title compound (66.9 g). In addition, the solvent in the obtained filtrate was evaporated, to the residue were added ethyl acetate (5 ml) and hexane (20 ml), and the mixture was stirred at room temperature for 1 hr. The precipitated solid was collected by filtration, and washed with hexane. The obtained solid was dried under reduced pressure to further give the title compound (2.5 g).

$^1$H-NMR (400 MHz, DMSO-$D_6$) δ: 8.01 (1H, d, J=7.6 Hz), 7.65-7.61 (2H, m), 7.37 (1H, t, J=7.6 Hz), 7.17-7.14 (2H, m), 4.13-4.05 (4H, m), 2.47 (2H, t, J=7.3 Hz), 2.02-1.95 (2H, m), 1.19 (3H, td, J=7.2, 0.7 Hz).

Step 6

Ethyl 4-[(9R)-4-chloro-9-hydroxy-9-(trifluoromethyl)-9H-fluoren-2-yloxy]butyrate

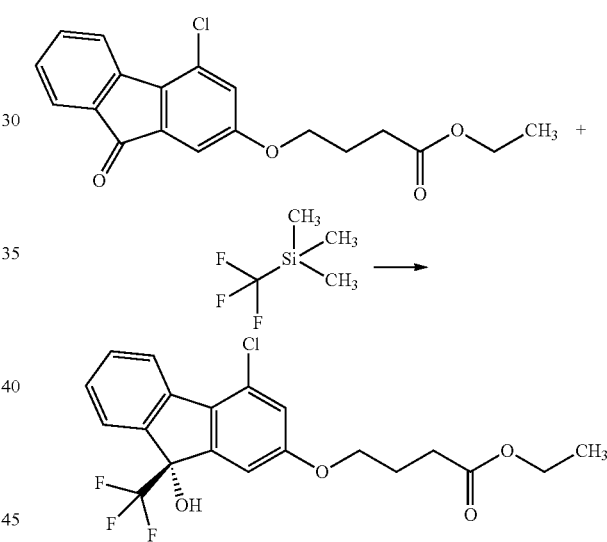

Under an argon atmosphere, ethyl 4-(4-chloro-9-oxo-9H-fluorene-2-yloxy)butyrate (69.4 g) was dissolved in THF (700 ml), and N-(4-tert-butylbenzyl)cinchonidium 4-methoxyphenoxide (6.4 g) was added. To the reaction mixture was added dropwise a solution of trimethyl(trifluoromethyl)silane (52.0 ml) in THF (140 ml) at −16° C., and the mixture was stirred at the same temperature for 15 min. To the reaction mixture were successively added acetic acid (23.0 ml) and 1M tetrabutylammonium fluoride/THF solution (222 ml), and the mixture was stirred at room temperature for 1 hr. The solvent in the reaction mixture was evaporated, and to the obtained residue were added toluene (500 ml) and saturated aqueous sodium hydrogen carbonate (200 ml) to allow for layer separation. The obtained organic layer was washed successively with saturated aqueous sodium hydrogen carbonate (150 ml, twice), 1N aqueous sodium hydroxide (100 ml), water (100 ml), 1N hydrochloric acid (100 ml), water (100 ml) and saturated brine (100 ml). To the obtained organic layer were added anhydrous magnesium sulfate and silica gel (150 g), and the mixture was stirred for 10 min. The insoluble material was filtered off, and the insoluble material was washed successively with toluene (300 ml) and ethyl acetate (800 ml). The obtained filtrate and the toluene washing were combined and the solvent was evaporated to give the title compound (72.1 g). Also, the solvent in the ethyl acetate washing was evaporated, to the obtained residue were added silica gel (40 g) and a mixed solvent of hexane and ethyl acetate (ethyl acetate:hexane 2:1, 300 ml), and the mixture was stirred at room temperature. The insoluble material was filtered off, and the insoluble material was washed with a mixed solvent of hexane and ethyl acetate (ethyl acetate:hexane=2:1, 300 ml). The solvent in the obtained filtrate was evaporated to further give the title compound (20.3 g).

$^1$H-NMR (400 MHz, DMSO-D$_6$) δ: 8.14 (1H, d, J=7.7 Hz), 7.66 (1H, d, J=7.5 Hz), 7.53 (1H, t, J=7.6 Hz), 7.42-7.38 (2H, m), 7.14 (2H, s), 4.11-4.05 (4H, m), 2.47 (2H, t, J=7.5 Hz), 2.03-1.96 (2H, m), 1.19 (3H, td, J=7.1, 0.8 Hz).

(Absolute Configuration)

Identification of the absolute configuration of 4-chloro-2-methyl-9-(trifluoromethyl)-9H-fluoren-9-ol in the after-mentioned step 10 confirmed that the title compound obtained in this step is an (R) form. The optical purity was 52.9% e.e. The optical purity was determined under the HPLC analysis condition 1. Retention time of (S) form 19.6 min, retention time of (R) form 23.0 min.

Step 7

4-[(9R)-4-Chloro-9-hydroxy-9-(trifluoromethyl)-9H-fluoren-2-yloxy]butyric acid

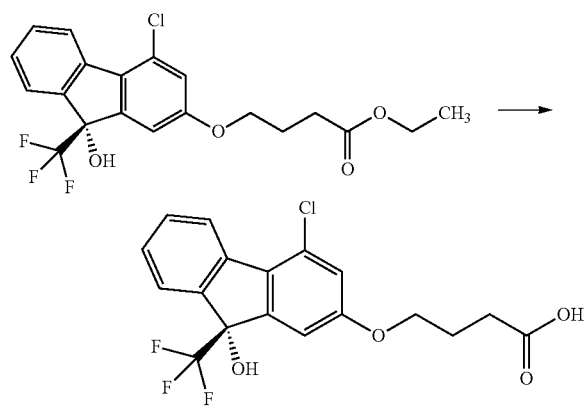

Ethyl 4-[(9R)-4-chloro-9-hydroxy-9-(trifluoromethyl)-9H-fluoren-2-yloxy]butyrate (92.2 g) was dissolved in ethanol (100 ml), 4N aqueous sodium hydroxide (100 ml) was added, and the mixture was stirred at 80° C. overnight. The reaction mixture was cooled to room temperature, water (200 ml) was added, and the mixture was washed twice with toluene (100 ml). The obtained aqueous layer was neutralized with concentrated hydrochloric acid (40 ml), and extracted twice with ethyl acetate (300 ml). The obtained ethyl acetate extract was washed successively with water (100 ml, twice), and saturated brine (100 ml), anhydrous magnesium sulfate and activated carbon (4.2 g) were added, and the mixture was stirred at room temperature for 10 min. The insoluble material was filtered off, and the solvent in the filtrate was evaporated. To the obtained residue was added chloroform (80 ml), and the mixture was heated to 50° C. Hexane (400 ml) was added dropwise, and the mixture was stirred at the same temperature for 30 min, and at room temperature for 2 hr. The precipitated solid was collected by filtration, washed with a mixed solvent of hexane and chloroform (hexane:chloroform=9:1, 50 ml), and dried under reduced pressure at 80° C. for 2 hr to give the title compound (72.5 g).

$^1$H-NMR (400 MHz, DMSO-D$_6$) δ: 12.17 (1H, br s), 8.14 (1H, d, J=7.7 Hz), 7.66 (1H, d, J=7.5 Hz), 7.54 (1H, td, J=7.7, 1.2 Hz), 7.42-7.30 (2H, m), 7.18-7.15 (2H, m), 4.09 (2H, t, J=6.4 Hz), 2.41 (2H, t, J=7.3 Hz), 2.00-1.93 (2H, m).

Step 8

(1S)-1-(4-Methylphenyl)ethylamine salt of 4-[(9R)-4-chloro-9-hydroxy-9-(trifluoromethyl)-9H-fluoren-2-yloxy]butyric acid

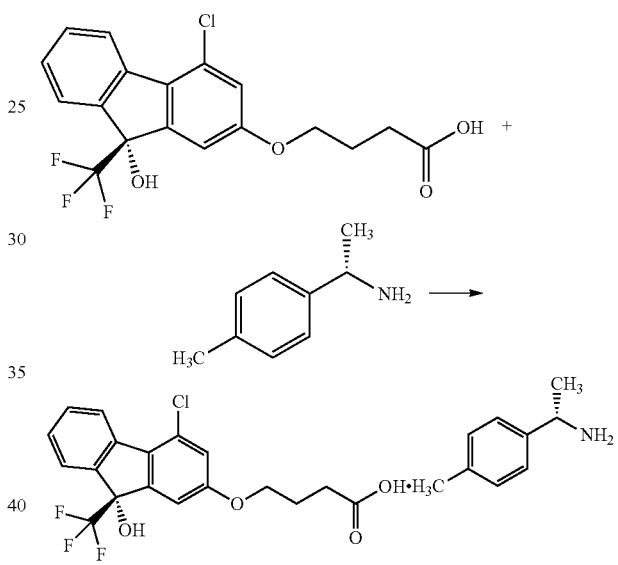

Under a nitrogen atmosphere, (1S)-1-(4-methylphenyl)ethylamine (19.5 g) was dissolved in ethyl acetate (720 ml), and 4-[(9R)-4-chloro-9-hydroxy-9-(trifluoromethyl)-9H-fluoren-2-yloxy]butyric acid (72.5 g) was added. The reaction mixture was stirred at 60° C. for 2 hr, and at room temperature overnight. The precipitated solid was collected by filtration, and washed with ethyl acetate (100 ml). The obtained solid was dried under reduced pressure at 60° C. for 5 hr to give the title compound (68.6 g). In addition, 4-[(9S)-4-chloro-9-hydroxy-9-(trifluoromethyl)-9H-fluoren-2-yloxy]butyric acid could be obtained from the filtrate.

(Optical Purity)

The optical purity of 4-[(9R)-4-chloro-9-hydroxy-9-(trifluoromethyl)-9H-fluoren-2-yloxy]butyric acid was determined under the HPLC analysis condition 1 (optical purity 90.2% e.e.). Retention time of (R) form 12.9 min, retention time of (S) form 10.4 min.

$^1$H-NMR (400 MHz, DMSO-D$_6$) δ: 8.14 (1H, d, J=7.7 Hz), 7.66 (1H, d, J=7.7 Hz), 7.53 (1H, td, J=7.6, 1.1 Hz), 7.40 (1H, td, J=7.6, 1.0 Hz), 7.26 (2H, d, J=7.9 Hz), 7.16-7.10 (4H, m), 4.08 (2H, t, J=6.5 Hz), 4.01 (1H, q, J=6.7 Hz), 2.32 (2H, t, J=7.3 Hz), 2.26 (3H, s), 1.98-1.91 (2H, m), 1.26 (3H, d, J=6.7 Hz).

Step 9

4-[(9R)-4-Chloro-9-hydroxy-9-(trifluoromethyl)-9H-fluoren-2-yloxy]butyric acid

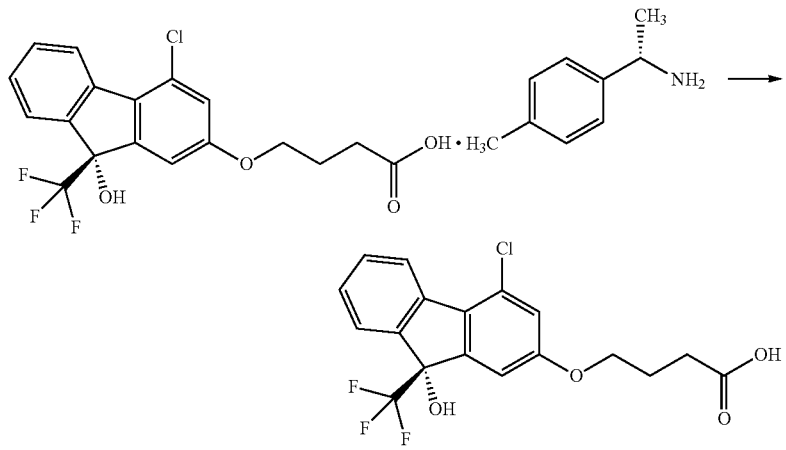

To (1S)-1-(4-methylphenyl)ethylamine salt of 4-[(9R)-4-chloro-9-hydroxy-9-(trifluoromethyl)-9H-fluoren-2-yloxy]butyric acid (68.6 g) were added ethyl acetate (500 ml) and 2N hydrochloric acid (300 ml), and the mixture was stirred at room temperature for 10 min. The mixture was allowed for layer separation. The obtained organic layer was washed successively with water (250 ml) and saturated brine (200 ml). The obtained organic layer was dried over anhydrous magnesium sulfate, the insoluble material was filtered off, and the solvent in the filtrate was evaporated to give the title compound (60.0 g).

$^1$H-NMR (400 MHz, DMSO-D$_6$) δ: 12.17 (1H, br s), 8.14 (1H, d, J=7.7 Hz), 7.66 (1H, d, J=7.5 Hz), 7.54 (1H, td, J=7.7, 1.2 Hz), 7.42-7.30 (2H, m), 7.18-7.15 (2H, m), 4.09 (2H, t, J=6.4 Hz), 2.41 (2H, t, J=7.3 Hz), 2.00-1.93 (2H, m).

Step 10

(9R)-4-Chloro-9-(trifluoromethyl)-9H-fluorene-2,9-diol

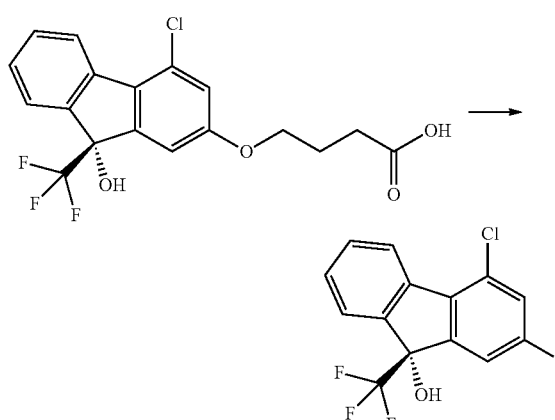

To 4-[(9R)-4-chloro-9-hydroxy-9-(trifluoromethyl)-9H-fluoren-2-yloxy]butyric acid (50 g) were added N-methylpyrrolidone (200 ml) and pyridine hydrochloride (298 g), and the mixture was stirred at an oil bath temperature of 200° C. for 2 days. The reaction mixture was cooled to room temperature, diluted with ethyl acetate (500 ml), and washed twice with water. The obtained aqueous layer was extracted again with ethyl acetate (300 ml). The combined organic layer was washed successively with water, 1N hydrochloric acid and saturated brine. To the obtained organic layer were added anhydrous magnesium sulfate and activated carbon (10 g), and the mixture was stirred at room temperature. The insoluble material was filtered off through celite. The solvent in the obtained organic layer was evaporated, hexane was added to the residue, and the mixture was stirred at room temperature. The precipitated solid was collected by filtration, and dried under reduced pressure at room temperature. The obtained crude product was dissolved in ethyl acetate (500 ml), washed 3 times with water, dried over anhydrous magnesium sulfate. The insoluble material was filtered off, and the solvent in the filtrate was evaporated. To the residue was added hexane, and the mixture was stirred at room temperature. The precipitated solid was collected by filtration, dried under reduced pressure at room temperature to give the title compound (22.4 g).

$^1$H-NMR (400 MHz, DMSO-D$_6$) δ: 10.37 (1H, br s), 8.09 (1H, d, J=7.5 Hz), 7.63 (1H, d, J=7.5 Hz), 7.50 (1H, td, J=7.6, 1.0 Hz), 7.36 (1H, td, J=7.6, 1.0 Hz), 7.32 (1H, br s), 7.06 (1H, s), 6.91 (1H, br d, J=2.0 Hz).

(Absolute Configuration)

The absolute configuration of the title compound was determined by HPLC analysis using the optically active column of compound (100A) and compound (100B) prepared in the following steps (Step A-1 to Step A-2 and Step B-1).

Step A-1

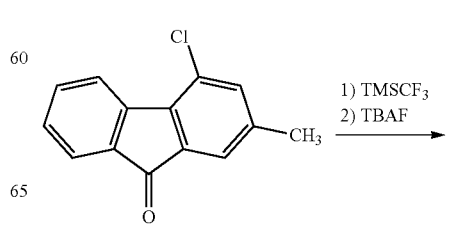

-continued

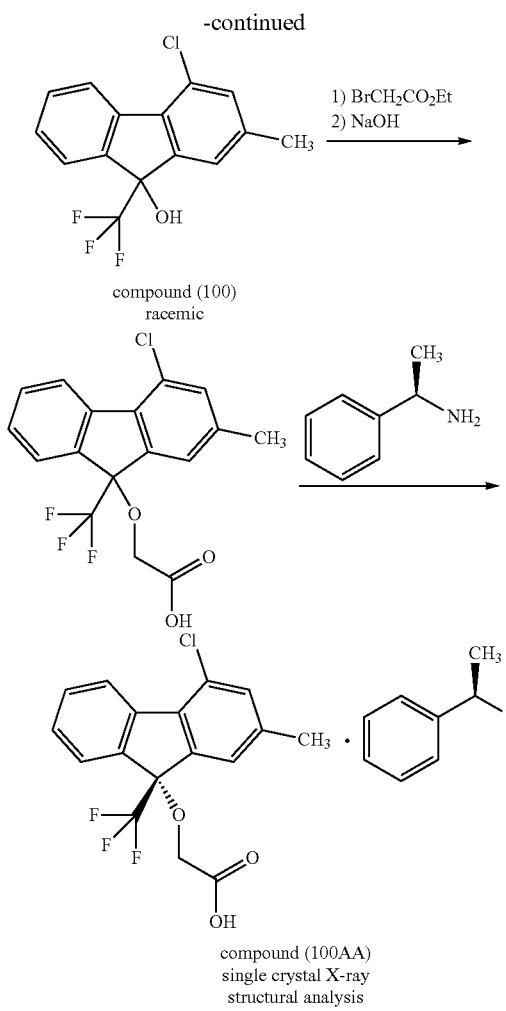

compound (100)
racemic compound (100AA)
single crystal X-ray
structural analysis 4-Chloro-2-methyl-9H-fluoren-9-one was subjected to trifluoromethylation, reaction with ethyl bromoacetate, and hydrolysis to give [4-chloro-2-methyl-9-(trifluoromethyl)-9H-fluorene-9-yloxy]acetic acid. This compound was optically resolved using (1R)-1-phenylethylamine, and the absolute configuration was determined to be (R) by single crystal X-ray structural analysis of the obtained (1R)-1-phenylethylamine salt (100AA).

Step A-2

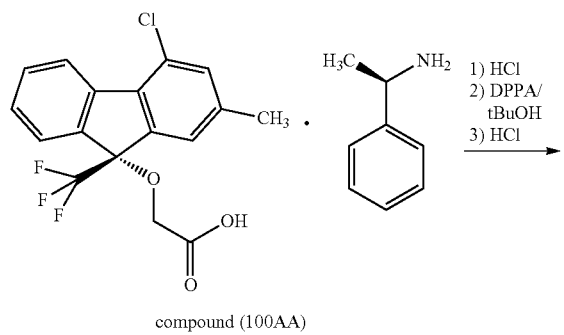

compound (100AA)

-continued

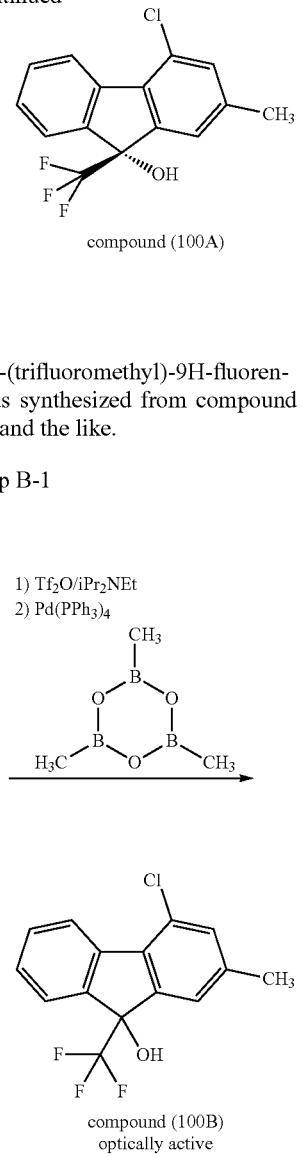

compound (100A)

(9R)-4-Chloro-2-methyl-9-(trifluoromethyl)-9H-fluoren-9-ol (compound (100A)) was synthesized from compound 100AA by an acid treatment and the like.

Step B-1 optically active compound (100B)
optically active

The hydroxyl group at the 2-position of 4-chloro-9-(trifluoromethyl)-9H-fluorene-2,9-diol obtained in step 10 was converted to a methyl group by the above-mentioned method to give 4-chloro-2-methyl-9-(trifluoromethyl)-9H-fluoren-9-ol (compound (100B)).

(HPLC Analysis Using Optically Active Column)

Both enantiomers of compound (100) were separated by HPLC using an optically active column (HPLC analysis condition 3). HPLC analysis of compound (100A) confirmed that the retention time of (R) form was 18.4 min, and the retention time of (S) form was 17.0 min. Compound (100A) and compound (100B) were analyzed under the HPLC condition to find that the retention time matches.

It is considered that the absolute configuration of the asymmetric carbon does not convert during the production of the above-mentioned compound (100A) and compound (100B). The results have confirmed that 4-chloro-9-(trifluoromethyl)-9H-fluorene-2,9-diol obtained in step 10 has an absolute configuration of (R).

Step 11

(9R)-4-Chloro-2-(3-hydroxy-3-methylbutyloxy)-9-(trifluoromethyl)-9H-fluoren-9-ol

Step 12

Ethyl 2-{4-[(9R)-9-hydroxy-2-(3-hydroxy-3-methyl-butyloxy)-9-(trifluoromethyl)-9H-fluoren-4-yl]-1H-pyrazol-1-yl}-2-methylpropionate

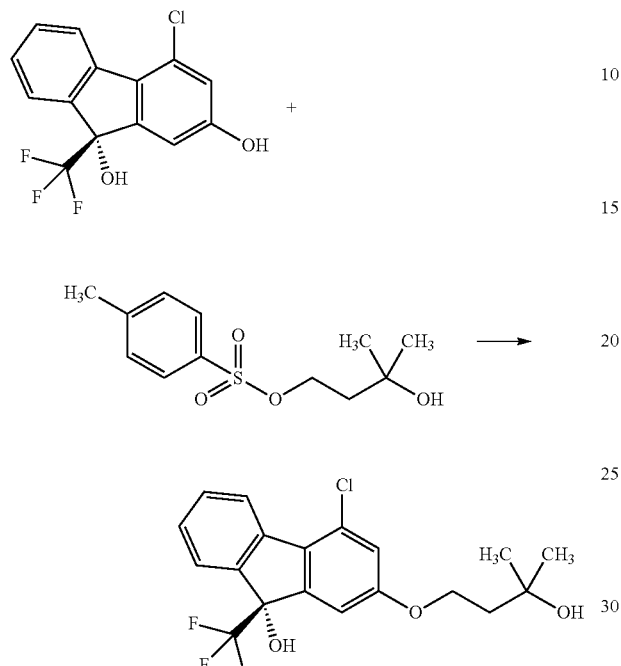

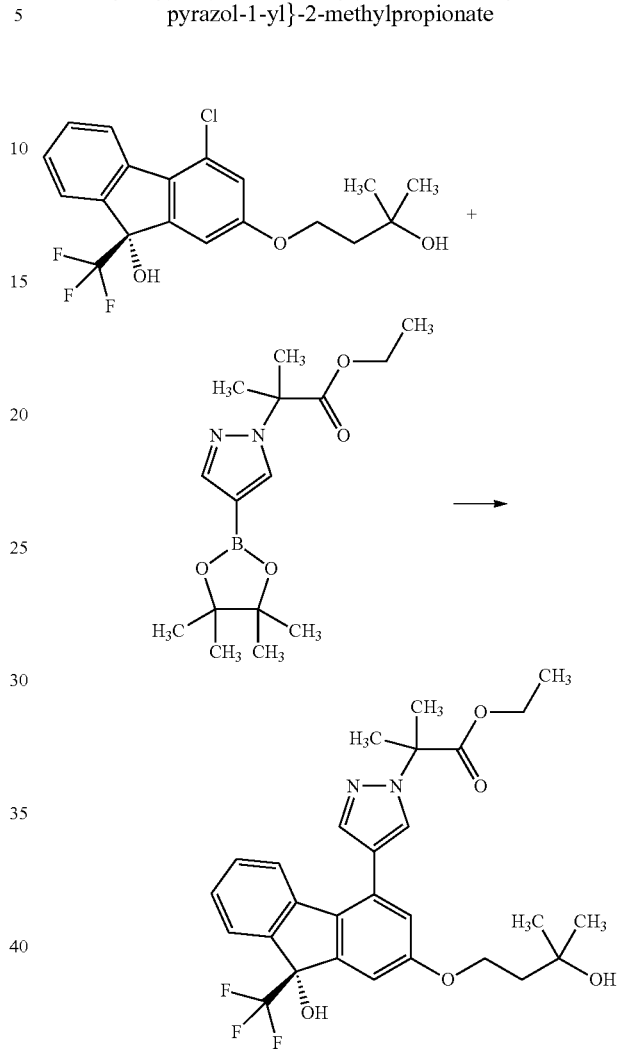

Under a nitrogen atmosphere, (9R)-4-chloro-9-(trifluoromethyl)-9H-fluorene-2,9-diol (55.5 g) was dissolved in N,N-dimethylformamide (550 ml), 3-hydroxy-3-methylbutyl toluene-4-sulfonate (49.6 g) and potassium carbonate (39.5 g) were added, and the mixture was stirred at an oil bath temperature of 70° C. overnight. To the reaction mixture was added a solution of 3-hydroxy-3-methylbutyl toluene-4-sulfonate (4.0 g) in N,N-dimethylformamide (5 ml), and the mixture was further stirred at the same temperature for 9.5 hr. The reaction mixture was ice-cooled, water (800 ml) was added, and the mixture was extracted with ethyl acetate (900 ml). The obtained organic layer was washed with water (500 ml, 3 times) and saturated brine (500 ml). The obtained organic layer was dried over anhydrous sodium sulfate, the insoluble material was filtered off, and the solvent in the filtrate was evaporated. The obtained residue was purified by silica gel column chromatography (a mixture of hexane and ethyl acetate was used as an elution solvent, first eluted with a mixture of (hexane:ethyl acetate) at a mixing ratio 3:1, and then with the mixture at a mixing ratio 2:1, and further with the mixture at a mixing ratio 3:2) to give the title compound (49.5 g).

$^1$H-NMR (400 MHz, DMSO-D$_6$) δ: 8.12 (1H, d, J=7.6 Hz), 7.64 (1H, d, J=7.4 Hz), 7.52 (1H, td, J=7.6, 0.9 Hz), 7.40-7.36 (2H, m), 7.15-7.13 (2H, m), 4.41 (1H,$), 4.16 (2H, t, J=7.1 Hz), 1.85 (2H, t, J=7.1 Hz), 1.17 (6H, s).

Under an argon atmosphere, (9R)-4-chloro-2-(3-hydroxy-3-methylbutyloxy)-9-(trifluoromethyl)-9H-fluoren-9-ol (49.5 g) was dissolved in toluene (445 ml), ethyl 2-methyl-2-[4-(4,4,5,5-tetramethyl[1,3,2]dioxaborolan-2-yl)-1H-pyrazol-1-yl]propionate (59.2 g), water (149 ml), tripotassium phosphate (54.3 g), palladium acetate (2.9 g) and 2-dicyclohexylphosphino-2',6'-dimethoxybiphenyl (SPhos) (10.5 g) were added, and the mixture was stirred at an oil bath temperature of 100° C. for 3.5 hr. The reaction mixture was cooled to room temperature, and water (300 ml) was added. The insoluble material was filtered off through celite, and the insoluble material was washed with toluene (150 ml) and water (50 ml). The obtained filtrates were combined to allow for layer separation. The obtained organic layer was washed successively with water (500 ml) and saturated brine (500 ml). The obtained organic layer was dried over anhydrous sodium sulfate, the insoluble material was filtered off, and the solvent in the filtrate was evaporated. The obtained residue was purified by silica gel column chromatography (a mixture of hexane and ethyl acetate was used as an elution solvent, first eluted with a mixture of (hexane:ethyl acetate) at a mixing ratio 2:1, and then with the mixture at a mixing ratio 1:1,

Step 13

2-{4-[(9R)-9-Hydroxy-2-(3-hydroxy-3-methylbuty-loxy)-9-(trifluoromethyl)-9H-fluoren-4-yl]-1H-pyrazol-1-yl}-2-methylpropionic acid

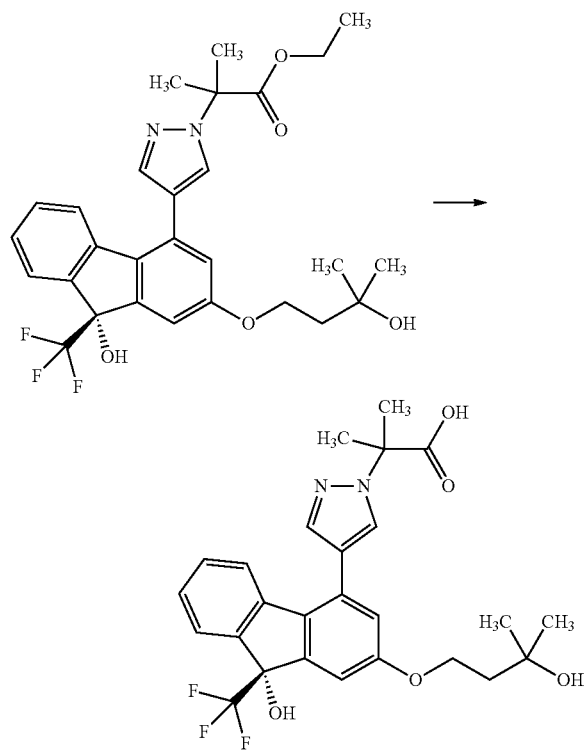

Ethyl 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropionate (68.4 g) was dissolved in ethanol (256 ml), 4N aqueous sodium hydroxide (128 ml) was added, and the mixture was stirred at room temperature for 2.5 hr. The reaction mixture was ice-cooled, 2N hydrochloric acid (333 ml) was added dropwise, and the mixture was extracted with ethyl acetate (500 ml). The obtained organic layer was washed successively with water (400 ml, twice) and saturated brine (400 ml). The obtained organic layer was dried over anhydrous sodium sulfate, the insoluble material was filtered off, and the solvent in the filtrate was evaporated to give the title compound (70.0 g).

$^1$H-NMR (400 MHz, DMSO-D$_6$) δ: 13.06 (1H, br s), 8.14 (1H, s), 7.62 (1H, s), 7.57 (1H, dd, J=6.4, 0.6 Hz), 7.27-7.19 (4H, m), 7.12 (1H, s), 6.84 (1H, d, J=2.3 Hz), 4.38 (1H, s), 4.14 (2H, t, J=7.2 Hz), 1.85 (2H, t, J=7.2 Hz), 1.82 (3H,$), 1.81 (3H, s), 1.16 (6H, s).

Step 14

2-{4-[(9R)-9-Hydroxy-2-(3-hydroxy-3-methylbutyloxy)-9-(trifluoromethyl)-9H-fluoren-4-yl]-1H-pyrazol-1-yl}-2-methylpropanamide (compound (2))

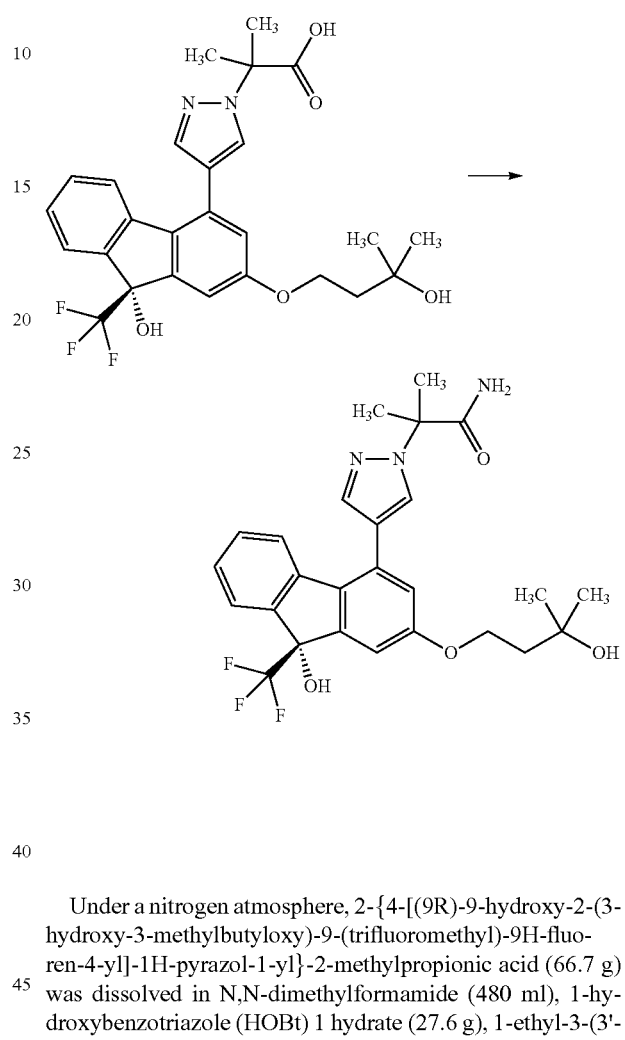

Under a nitrogen atmosphere, 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropionic acid (66.7 g) was dissolved in N,N-dimethylformamide (480 ml), 1-hydroxybenzotriazole (HOBt) 1 hydrate (27.6 g), 1-ethyl-3-(3'-dimethylaminopropyl)carbodiimide (WSC) hydrochloride (34.6 g) and 28% aqueous ammonia (24.5 ml) were added, and the mixture was stirred at room temperature overnight. The reaction mixture was ice-cooled, water (630 ml) and 2N hydrochloric acid (330 ml) were added dropwise, and the mixture was extracted with ethyl acetate (800 ml). The obtained aqueous layer was extracted again with ethyl acetate (500 ml). The obtained organic layers were combined, and washed successively with water (500 ml, twice), saturated aqueous sodium hydrogen carbonate (500 ml), and saturated brine (500 ml). The obtained organic layer was dried over anhydrous sodium sulfate, the insoluble material was filtered off, and the solvent in the filtrate was evaporated to give the title compound (60.0 g).

$^1$H-NMR (400 MHz, DMSO-D$_6$) δ: 8.08 (1H, s), 7.66 (1H, s), 7.58-7.56 (1H, m), 7.32-7.30 (1H, m), 7.25-7.22 (4H, m), 7.12 (1H, br s), 6.96 (1H, br s), 6.87 (1H, d, J=2.3 Hz), 4.38 (1H, s), 4.14 (2H, t, J=7.2 Hz), 1.85 (2H, t, J=7.2 Hz), 1.78 (3H, s), 1.78 (3H, s), 1.17 (6H, s).

Step 15

2-{4-[(9R)-9-Hydroxy-2-(3-hydroxy-3-methylbutyloxy)-9-(trifluoromethyl)-9H-fluoren-4-yl]-1H-pyrazol-1-yl}-2-methylpropanamide monohydrate (compound (2h))

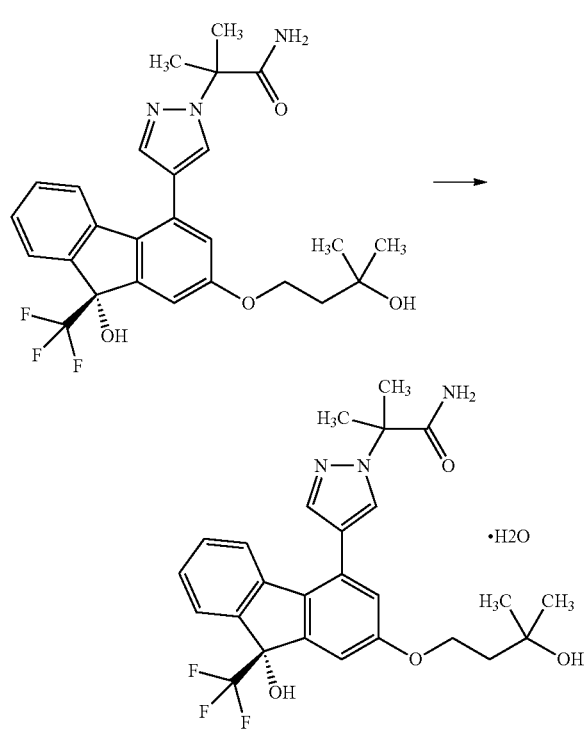 [SMILES: CC(C)(O)CCOc1cc(-c2cnn(C(C)(C)C(=O)O)c2)c2c(c1)[C@@](O)(C(F)(F)F)c1ccccc1-2 ; CC(C)(O)CCOc1cc(-c2cnn(C(C)(C)C(N)=O)c2)c2c(c1)[C@@](O)(C(F)(F)F)c1ccccc1-2]

2-{4-[(9R)-9-Hydroxy-2-(3-hydroxy-3-methylbutyloxy)-9-(trifluoromethyl)-9H-fluoren-4-yl]-1H-pyrazol-1-yl}-2-methylpropanamide (compound (2)) (60.0 g) obtained in the previous step was dissolved in ethyl acetate (109 ml), water (2 ml) was added, and the mixture was heated to 50° C. To this mixture were successively added dropwise hexane (226 ml), and a mixed solvent of hexane and ethyl acetate (hexane:ethyl acetate 2:1, 150 ml), and the mixture was allowed to cool to room temperature and stirred overnight. The precipitated solid was collected by filtration, and washed with a mixed solvent of hexane and ethyl acetate (hexane:ethyl acetate=2:1, 180 ml). The obtained solid was dried under reduced pressure at room temperature overnight to give the title compound (52.2 g, optical purity 98.6% e.e.). The optical purity was determined under the HPLC analysis condition 2. Retention time of (R) form 11.3 min, retention time of (S) form 13.9 min. Specific optical rotation [α]p+37.9° (c=1.01 MeOH 25° C.)

$^1$H-NMR (400 MHz, DMSO-D$_6$) δ: 8.08 (1H, s), 7.66 (1H, s), 7.58-7.56 (1H, m), 7.32-7.30 (1H, m), 7.25-7.22 (4H, m), 7.12 (1H, br s), 6.96 (1H, br s), 6.87 (1H, d, J=2.3 Hz), 4.38 (1H, s), 4.14 (2H, t, J=7.2 Hz), 1.85 (2H, t, J=7.2 Hz), 1.78 (3H, s), 1.78 (3H, s), 1.17 (6H, s).

(Elemental Analysis Measurement)

The results of the elemental analysis matched well with the theoretical value of compound (2h) calculated.

Calculated: C, 59.88; H, 5.80; N, 8.06 (Calculated as monohydrate)

Found: C, 59.86; H, 5.74; N, 8.00.

Step 16

2-{4-[(9R)-9-Hydroxy-2-(3-hydroxy-3-methylbutyloxy)-9-(trifluoromethyl)-9H-fluoren-4-yl]-1H-pyrazol-1-yl}-2-methylpropanamide (compound (2))

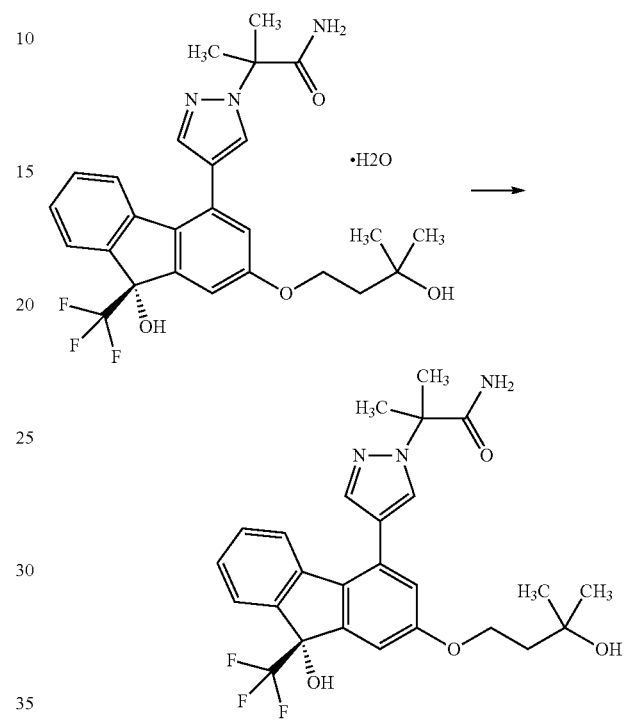

To 2-{4-[(9R)-9-hydroxy-2-(3-hydroxy-3-methylbutyloxy)-9-(trifluoromethyl)-9H-fluoren-4-yl]-1H-pyrazol-1-yl}-2-methylpropanamide monohydrate (compound (2h)) (22.63 g) obtained in the previous step was added toluene (340 ml). The reaction mixture was stirred at an oil bath temperature of 130° C. for 2 hr under a nitrogen atmosphere with removing water by a Dean-Stark apparatus. The reaction mixture was further stirred at an oil bath temperature of 70° C. for 1.5 hr, allowed to cool to room temperature, and stirred overnight. The precipitated solid was collected by filtration, and washed with toluene (100 ml). The obtained solid was dried under reduced pressure at room temperature for 3 days, and further dried under reduced pressure at 60° C. for 1 day to give the title compound (21.5 g).

$^1$H-NMR (400 MHz, DMSO-D$_6$) δ: 8.08 (1H, s), 7.66 (1H, s), 7.58-7.56 (1H, m), 7.32-7.30 (1H, m), 7.25-7.22 (4H, m), 7.12 (1H, br s), 6.96 (1H, br s), 6.87 (1H, d, J=2.3 Hz), 4.38 (1H, s), 4.14 (2H, t, J=7.2 Hz), 1.85 (2H, t, J=7.2 Hz), 1.78 (3H, s), 1.78 (3H, s), 1.17 (6H, s).

(Elemental Analysis Measurement)

The results of the elemental analysis matched well with the theoretical value of compound (2) calculated.

Calculated: C, 62.02; H, 5.61; N, 8.35 (Calculated as anhydrous)

Found: C, 62.17; H, 5.60; N, 8.47.

Step C-1

Preparation of N-(4-tert-butylbenzyl)cinchonidium bromide

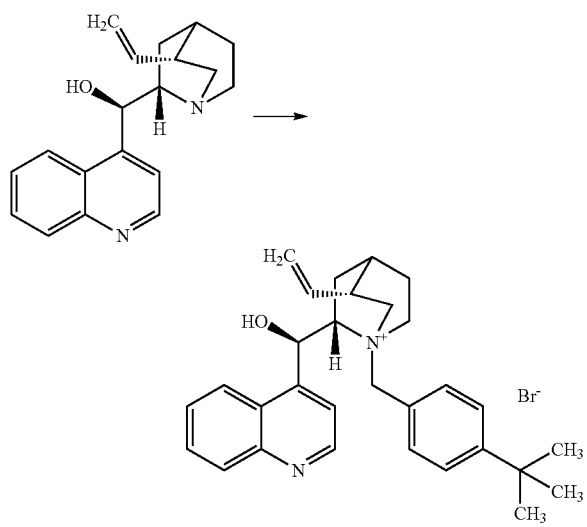

Cinchonidine (10.6 g) was dissolved in tetrahydrofuran (200 ml), 4-tert-butylbenzylbromide (10.1 g) and tetrabutylammonium iodide (0.66 g) were added, and the mixture was stirred at 70° C. overnight. The reaction mixture was cooled to room temperature, the solid was collected by filtration, and washed with ethyl acetate (50 ml). The obtained solid was dried under reduced pressure overnight to give the title compound (18.5 g).

$^1$H-NMR (400 MHz, DMSO-D$_6$) δ: 8.99 (1H, d, J=4.4 Hz), 8.27 (1H, d, J=8.2 Hz), 8.11 (1H, dd, J=8.5, 1.0 Hz), 7.89-7.79 (2H, m), 7.78-7.71 (1H, m), 7.63 (2H, d, J=8.4 Hz), 7.59 (2H, t, J=8.4 Hz), 6.72 (1H, d, J=4.2 Hz), 6.57-6.51 (1H, br s), 5.67 (1H, ddd, J=17.0, 10.4, 6.4 Hz), 5.14 (1H, d, J=17.2 Hz), 5.08 (1H, d, J=12.6 Hz), 5.00-4.90 (2H, m), 4.30-4.18 (1H, m), 3.91 (1H, t, J=8.7 Hz), 3.74-3.64 (1H, m), 3.35-3.18 (2H, m), 2.76-2.65 (1H, m), 2.18-1.94 (3H, m), 1.90-1.78 (1H, m), 1.40-1.22 (1H, m), 1.34 (9H, s).

Step C-2

Preparation of N-(4-tert-butylbenzyl)cinchonidium 4-methoxyphenoxide

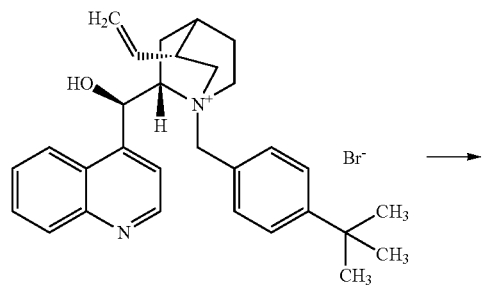

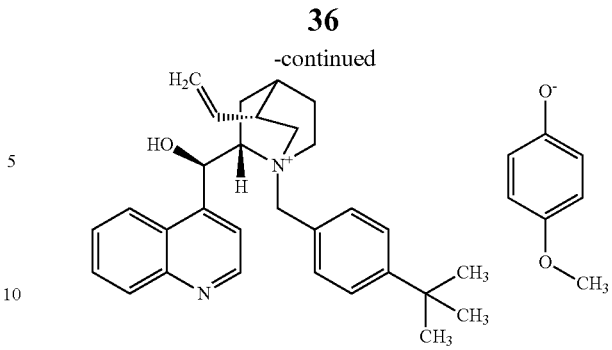

N-(4-tert-Butylbenzyl)cinchonidium bromide (18.5 g), AMBERLYST® A26 (strong basic ion exchange resin of styrene, divinylbenzene matrix) (18.5 g) and methanol (280 ml) were added, and the mixture was stirred at room temperature overnight. The insoluble material was filtered off through celite, and washed with methanol (100 ml). To the filtrate was added 4-methoxyphenol (4.8 g), and the solvent was evaporated. The residue was azeotropically evaporated 3 times with toluene (100 ml), and toluene (20 ml) was added. Then, diisopropyl ether (200 ml) was added dropwise, and the mixture was stirred at room temperature for 3 hr. The precipitated solid was collected by filtration, washed with diisopropyl ether (50 ml) and the mixture was dried under reduced pressure at room temperature overnight to give the title compound (21.8 g).

$^1$H-NMR (400 MHz, DMSO-D$_6$) δ: 8.91 (1H, d, J=4.4 Hz), 8.17 (1H, d, J=8.2 Hz), 8.07 (1H, d, J=8.4 Hz), 7.89 (1H, d, J=4.4 Hz), 7.79 (1H, t, J=7.6 Hz), 7.64 (1H, t, J=7.5 Hz), 7.57-7.52 (5H, m), 6.56-6.55 (2H, m), 6.43-6.42 (3H, m), 5.67-5.59 (1H, m), 5.28 (1H, d, J=12.1 Hz), 5.12 (1H, d, J=17.2 Hz), 4.92 (1H, d, J=10.6 Hz), 4.84 (1H, d, J=12.1 Hz), 4.65-4.53 (1H, m), 3.80 (1H, t, J=8.8 Hz), 3.65-3.63 (1H, m), 3.57 (3H, s), 3.25 (1H, t, J=11.6 Hz), 3.10-3.07 (1H, m), 2.67 (1H, br s), 2.07-2.02 (2H, m), 1.95 (1H, br s), 1.79-1.76 (1H, br m), 1.33 (9H, s), 1.16-1.11 (1H, m).

Step D

Preparation of 3-hydroxy-3-methylbutyl toluene-4-sulfonate

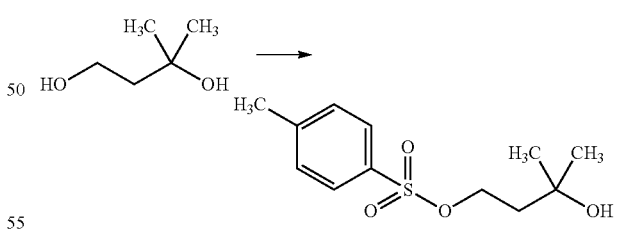

Under a nitrogen atmosphere, 3-methylbutane-1,3-diol (300 g) was dissolved in pyridine (900 ml), and a solution of 4-methylbenzenesulfonyl chloride (500 g) in toluene (900 ml) and acetonitrile (125 ml) was added dropwise over 2 hr. The reaction mixture was stirred at room temperature for 4 hr, and toluene (500 ml) and water (1800 ml) were added to allow for layer separation. The obtained organic layer was washed successively with aqueous sulfuric acid and water (twice). The solvent in the obtained organic layer was evaporated, and the residue was azeotropically evaporated with toluene (500 ml) to give the title compound (535 g).

¹H-NMR (CDCl₃) δ: 7.81-7.76 (2H, m), 7.36-7.31 (2H, m), 4.20 (2H, td, J=6.8, 1.6 Hz), 2.44 (3H, s), 1.85 (2H, td, J=6.8, 1.6 Hz), 1.33 (1H, s), 1.21 (6H, s).

Example 2

Synthesis of 2-{4-[(9R)-9-hydroxy-2-(4-hydroxy-4-methylpentyloxy)-9-(trifluoromethyl)-9H-fluoren-4-yl]-1H-pyrazol-1-yl}-2-methylpropanamide (compound (3))

Step 1

Ethyl 4-[(9R)-4-chloro-9-hydroxy-9-(trifluoromethyl)-9H-fluoren-2-yloxy]butyrate

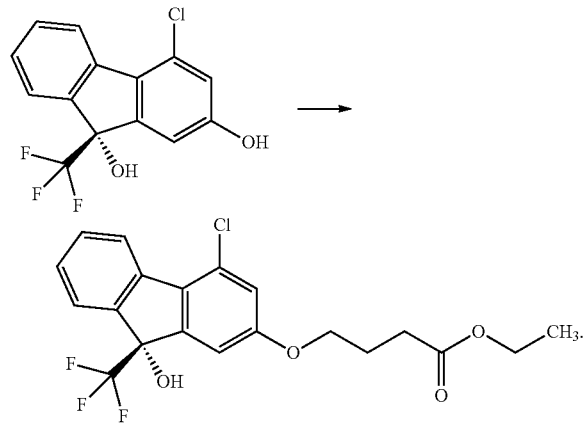

(9R)-4-Chloro-9-(trifluoromethyl)-9H-fluorene-2,9-diol (200 mg) obtained in step 10 of example 1 was dissolved in N,N-dimethylformamide (2 ml), potassium carbonate (185 mg) and ethyl 4-bromobutyrate (105 μl) were added, and the mixture was stirred at room temperature for 7 hr. To the reaction mixture was added water, and the mixture was extracted twice with ethyl acetate. The obtained organic layer was washed successively with water (twice) and saturated brine. The obtained organic layer was dried over anhydrous magnesium sulfate, the insoluble material was filtered off, and the solvent in the filtrate was evaporated. The obtained residue was purified by silica gel column chromatography (a mixture of hexane and ethyl acetate was used as an elution solvent, first eluted with a mixture at a mixing ratio 5:1 (hexane:ethyl acetate), then successively with a mixture at a mixing ratio 3:1, and further with a mixture at a mixing ratio 2:1) to give the title compound (197 mg).

¹H-NMR (400 MHz, CDCl₃) δ: 8.19 (1H, d, J=7.7 Hz), 7.66 (1H, d, J=7.7 Hz), 7.46 (1H, td, J=7.6, 1.0 Hz), 7.32 (1H, td, J=7.6, 1.0 Hz), 7.16 (1H, br s), 6.93 (1H, d, J=2.1 Hz), 4.14 (2H, q, J=7.1 Hz), 4.05 (2H, t, J=7.1 Hz), 2.82 (1H, s), 2.50 (2H, t, J=7.1 Hz), 2.15-2.06 (2H, m), 1.25 (3H, t, J=7.1 Hz).

Step 2

(9R)-4-Chloro-2-(4-hydroxy-4-methylpentyloxy)-9-(trifluoromethyl)-9H-fluoren-9-ol

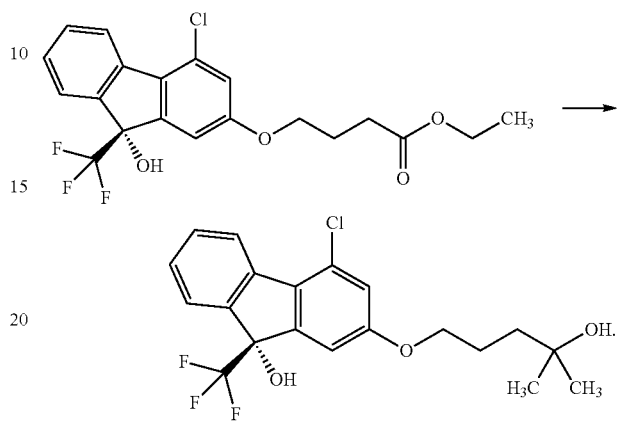

Under a nitrogen atmosphere, ethyl 4-[(9R)-4-chloro-9-hydroxy-9-(trifluoromethyl)-9H-fluoren-2-yloxy]butyrate (197 mg) was dissolved in THF (2 ml), and methyllithium/diethyl ether solution (1.07 M, 2.2 ml) was added dropwise at 0° C. The reaction mixture was stirred at the same temperature for 2 hr, water was added, and the mixture was extracted with ethyl acetate (twice). The obtained organic layer was washed successively with water (twice) and saturated brine. The obtained organic layer was dried over anhydrous magnesium sulfate, the insoluble material was filtered off, and the solvent in the filtrate was evaporated. The obtained residue was purified by silica gel column chromatography (a mixture of hexane and ethyl acetate was used as an elution solvent, first eluted with a mixture at a mixing ratio 3:1 (hexane:ethyl acetate), then with a mixture at a mixing ratio 2:1) to give the title compound (169 mg).

¹H-NMR (400 MHz, CDCl₃) δ: 8.19 (1H, d, J=7.7 Hz), 7.66 (1H, d, J=7.7 Hz), 7.47 (1H, td, J=7.7, 1.0 Hz), 7.32 (1H, td, J=7.7, 1.0 Hz), 7.17 (1H, br s), 6.93 (1H, d, J=2.3 Hz), 4.02 (2H, t, J=6.4 Hz), 2.82 (1H, s), 1.92-1.85 (2H, m), 1.65-1.62 (2H, m), 1.26 (3H, s), 1.25 (3H, s).

Step 3

Ethyl 2-{4-[(9R)-9-hydroxy-2-(4-hydroxy-4-methylpentyloxy)-9-(trifluoromethyl)-9H-fluoren-4-yl]-1H-pyrazol-1-yl}-2-methylpropionate

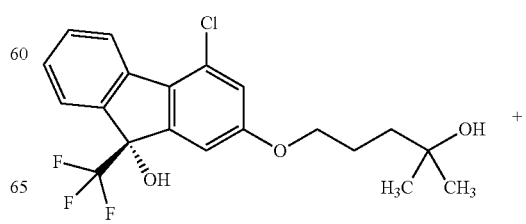

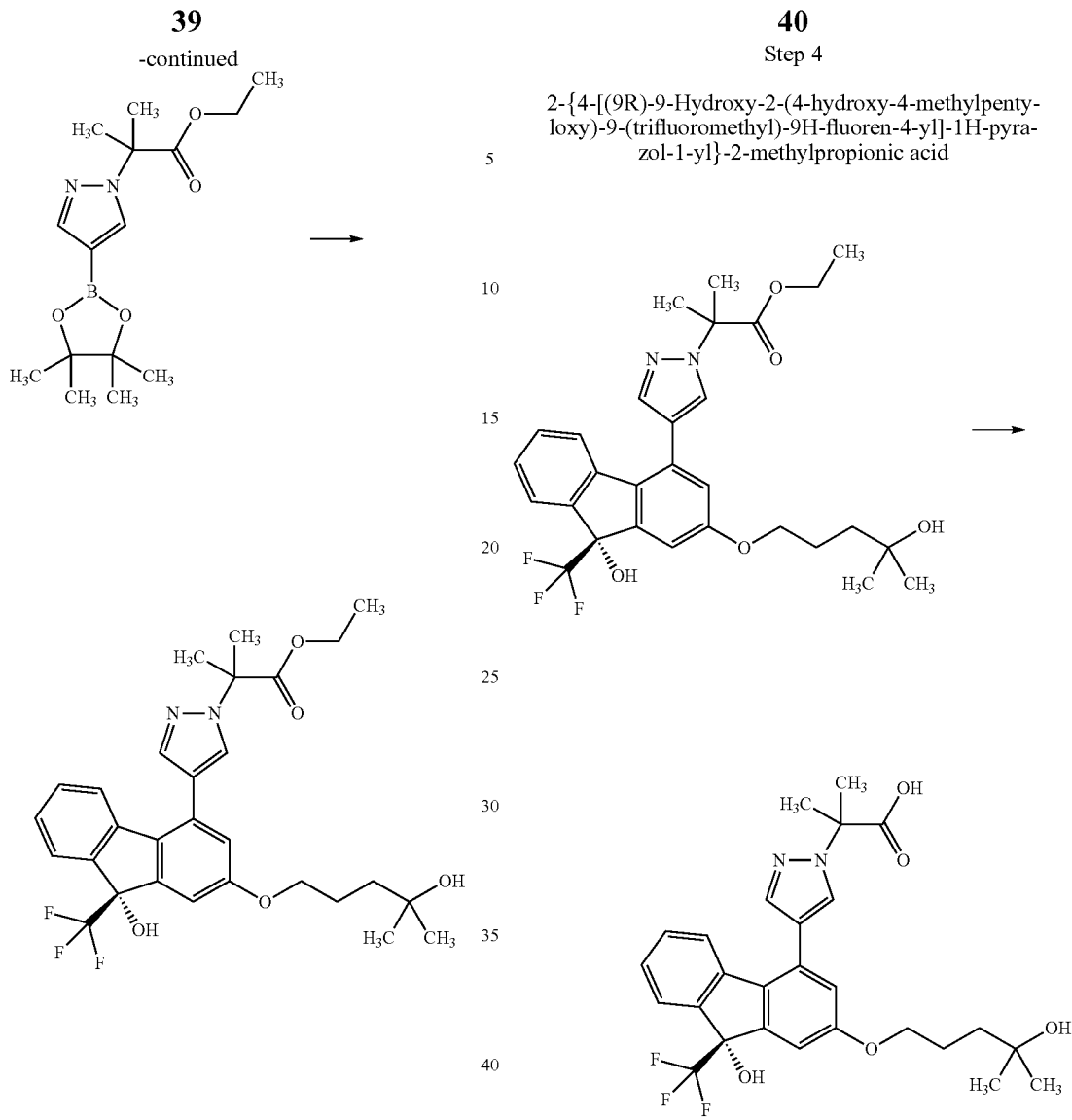

Step 4

2-{4-[(9R)-9-Hydroxy-2-(4-hydroxy-4-methylpentyloxy)-9-(trifluoromethyl)-9H-fluoren-4-yl]-1H-pyrazol-1-yl}-2-methylpropionic acid Under an argon atmosphere, (9R)-4-chloro-2-(4-hydroxy-4-methylpentyloxy)-9-(trifluoromethyl)-9H-fluoren-9-ol (169 mg) was dissolved in 1,4-dioxane (1.5 ml), ethyl 2-methyl-2-[4-(4,4,5,5-tetramethyl[1,3,2]dioxaborolan-2-yl)-1H-pyrazol-1-yl]propionate (194 mg), water (0.5 ml), tripotassium phosphate (178 mg), palladium acetate (9 mg), and SPhos (33 mg) were added, and the mixture was stirred at 100° C. for 4.5 hr. The reaction mixture was cooled to room temperature, water was added, and the mixture was extracted with ethyl acetate (twice). The obtained organic layer was washed successively with water (twice) and saturated brine. The obtained organic layer was dried over anhydrous magnesium sulfate, the insoluble material was filtered off, and the solvent in the filtrate was evaporated. The obtained residue was purified by silica gel column chromatography (a mixture of hexane and ethyl acetate at a mixing ratio 1:1 (hexane:ethyl acetate) was used as an elution solvent) to give the title compound (218 mg).

$^1$H-NMR (400 MHz, CDCl$_3$) δ: 7.69 (1H, s), 7.63-7.62 (2H, m), 7.21-7.19 (4H, m), 6.81 (1H, d, J=2.3 Hz), 4.21 (2H, q, J=7.1 Hz), 4.04 (2H, t, J=6.3 Hz), 2.82 (1H, s), 1.92 (3H, s), 1.91 (3H, s), 1.89-1.88 (2H, m), 1.66-1.64 (2H, m), 1.26 (6H, s), 1.26-1.23 (3H, m).

Ethyl 2-{4-[(9R)-9-hydroxy-2-(4-hydroxy-4-methylpentyloxy)-9-(trifluoromethyl)-9H-fluoren-4-yl]-1H-pyrazol-1-yl}-2-methylpropionate (218 mg) was dissolved in ethanol (2.2 ml), 4N aqueous sodium hydroxide (320 μl) was added, and the mixture was stirred at room temperature overnight. The reaction mixture was neutralized with 1N hydrochloric acid, and extracted with ethyl acetate (twice). The obtained organic layer was washed successively with water (twice) and saturated brine. The obtained organic layer was dried over anhydrous magnesium sulfate, the insoluble material was filtered off, and the solvent in the filtrate was evaporated to give the title compound (179 mg).

$^1$H-NMR (400 MHz, CDCl$_3$) δ: 7.73 (1H, s), 7.68 (1H, s), 7.63-7.62 (1H, m), 7.23-7.09 (4H, m), 6.78 (1H, d, J=2.6 Hz), 4.02 (2H, t, J=6.3 Hz), 1.93 (6H, s), 1.89-1.86 (2H, m), 1.65-1.61 (2H, m), 1.25 (6H, s).

Step 5

2-{4-[(9R)-9-Hydroxy-2-(4-hydroxy-4-methylpentyloxy)-9-(trifluoromethyl)-9H-fluoren-4-yl]-1H-pyrazol-1-yl}-2-methylpropanamide (compound (3))

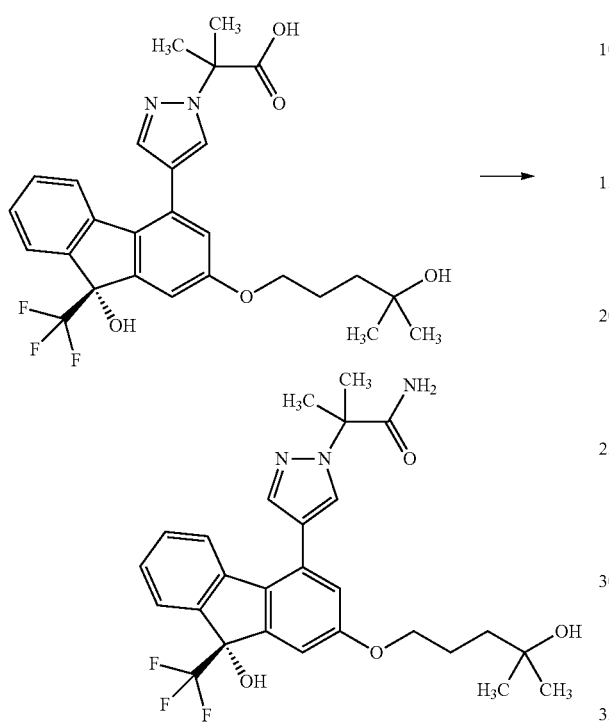

Under a nitrogen atmosphere, 2-{4-[(9R)-9-hydroxy-2-(4-hydroxy-4-methylpentyloxy)-9-(trifluoromethyl)-9H-fluoren-4-yl]-1H-pyrazol-1-yl}-2-methylpropionic acid (89 mg) was dissolved in N,N-dimethylformamide (1 ml), ammonium chloride (28 mg), N,N-diisopropylethylamine (148 μl) and 1-[bis(dimethylamino)methylene]-1H-1,2,3-triazolo[4,5-b]pyridin-1-ium 3-oxide hexafluorophosphate (HATU) (99 mg) were added, and the mixture was stirred at room temperature overnight. To the reaction mixture was added water, and the mixture was extracted with ethyl acetate (twice). The obtained organic layer was washed successively with diluted brine (twice) and saturated brine. The obtained organic layer was dried over anhydrous magnesium sulfate, the insoluble material was filtered off, and the solvent in the filtrate was evaporated. The obtained residue was purified by silica gel thin layer chromatography (a mixture of chloroform and methanol at a mixing ratio 9:1 (chloroform:methanol) was used as an elution solvent) to give the title compound (48 mg, optical purity 96.9% e.e.). The optical purity was determined under the HPLC analysis condition 2. Retention time of (R) form 13.0 min, retention time of (S) form 14.4 min.

Specific optical rotation $[\alpha]_D$ +37.5° (c=1.04 MeOH 25° C.)

$^1$H-NMR (400 MHz, DMSO-D$_6$) δ: 8.07 (1H, s), 7.66 (1H, s), 7.57-7.55 (1H, m), 7.34-7.31 (1H, m), 7.24-7.23 (3H, m), 7.18 (1H, s), 7.11 (1H, br s), 6.94 (1H, br s), 6.86 (1H, d, J=2.3 Hz), 4.16 (1H, s), 4.03 (2H, t, J=6.5 Hz), 1.80 (3H, s), 1.79 (3H, s), 1.80-1.75 (2H, m), 1.51-1.47 (2H, m), 1.11 (6H, s).

Preparation Example of Crystal of Compound (3)

To compound (3) (40 mg) synthesized by the above-mentioned example steps was added a mixture of MeOH and water (volume ratio 1:3 (0.5 mL)). Then, to this solution was added a crystal (0.5 mg) of compound (2h) and the mixture was stirred at room temperature for 3 days. The precipitated solid was collected by filtration to give a crystal (41 mg) of compound (3).

Preparation of Compounds (A), (B), (C) and (D)

Compound (A), compound (B), compound (C) and compound (D), which are represented by the following formulas, were each obtained as an optically active form according to the production method described in WO 2010/041748.

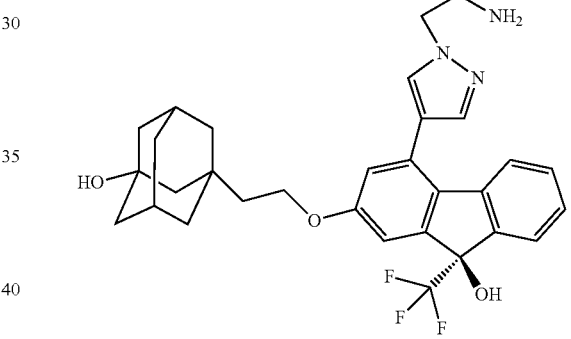

Compound (A)

2-(4-{(9R)-9-Hydroxy-2-[2-(3-hydroxyadamantan-1-yl)ethoxy]-9-(trifluoromethyl)-9H-fluoren-4-yl}-1H-pyrazol-1-yl)acetamide

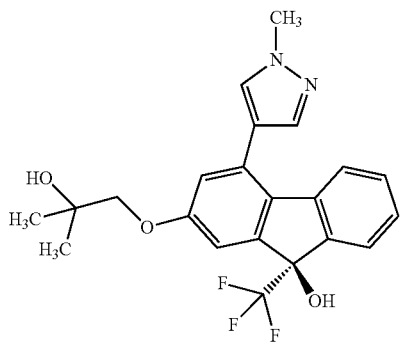 [SMILES: Cn1cc(-c2cc(OCC(C)(C)O)cc3c2-c2ccccc2[C@]3(O)C(F)(F)F)cn1]

Compound (B)

(9R)-2-(2-Hydroxy-2-methylpropoxy)-4-(1-methyl-1H-pyrazol-4-yl)-9-(trifluoromethyl)-9H-fluoren-9-ol

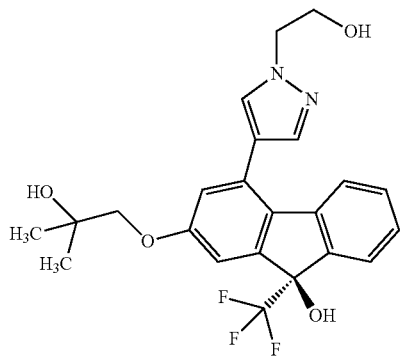 [SMILES: CC(C)(O)COc1cc(-c2cnn(CCO)c2)c2c(c1)[C@@](O)(C(F)(F)F)c1ccccc1-2]

Compound (C)

(9R)-4-[1-(2-Hydroxyethyl)-1H-pyrazol-4-yl]-2-(2-hydroxy-2-methylpropoxy)-9-(trifluoromethyl)-9H-fluoren-9-ol

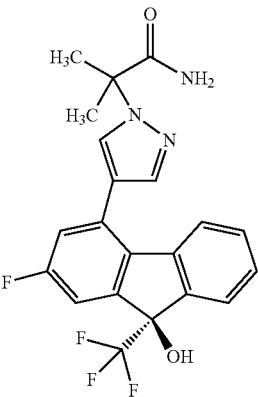 [SMILES: CC(C)(C(N)=O)n1cc(-c2cc(F)cc3c2-c2ccccc2[C@]3(O)C(F)(F)F)cn1]

Compound (D)

2-{4-[(9R)-2-Fluoro-9-hydroxy-9-(trifluoromethyl)-9H-fluoren-4-yl]-1H-pyrazol-1-yl}-2-methylpropanamide As a Formulation Example of the present invention, the following preparation can be mentioned. However, the present invention is not limited by these Formulation Examples.

Formulation Example 1

Production of Capsule

| | | |
|---|---|---|
| 1) compound of Example 1 (compound (2)) | 30 mg |
| 2) microcrystalline cellulose | 10 mg |
| 3) lactose | 19 mg |
| 4) magnesium stearate | 1 mg |

1), 2), 3) and 4) are mixed and filled in a gelatin capsule.

Formulation Example 2

Production of Tablet

| | | |
|---|---|---|
| 1) compound of Example 1 (compound (2)) | 10 g |
| 2) lactose | 50 g |
| 3) cornstarch | 15 g |
| 4) carmellose calcium | 44 g |
| 5) magnesium stearate | 1 g |

The total amount of 1), 2), 3) and 30 g of 4) are kneaded with water, vacuum dried, and sieved. The sieved powder is mixed with 14 g of 4) and 1 g of 5), and the mixture is punched by a tableting machine. In this way, 1000 tablets each containing 10 mg of the compound of Example 1 (compound (2)) per tablet are obtained.

Experimental Example 1

Inhibitory Action of PDHK Activity In Vitro

The inhibitory action of PDHK activity was assessed indirectly by measuring the residual PDH activity after kinase reaction in the presence of a test compound.

(Inhibitory Action of PDHK1 Activity)

In the case of human PDHK1 (hPDHK1, Genbank Accession No. L42450.1), a 1.3 kbp fragment encoding this protein was isolated from human liver cDNA by polymerase chain reaction (PCR). Modified hPDHK1 cDNA wherein FLAG-Tag sequence was added to the N terminus was prepared by PCR and cloned into a vector (pET17b-Novagen). The recombinant construct was transformed into Escherichia coli (DH5α-TOYOBO). The recombinant clones were identified, and plasmid DNA was isolated and subjected to the DNA sequence analysis. One clone which had the expected nucleic acid sequence was selected for expression work.

For expression of hPDHK1 activity, Escherichia coli strain BL21(DE3) cells (Novagen) were transformed with the pET17b vector containing modified hPDHK1 cDNA. The Escherichia coli were grown to an optical density 0.6 (600 nmol/L) at 30° C. Protein expression was induced by the addition of 500 µmol/L isopropyl-β-thiogalactopyranoside. The Escherichia coli were cultured at 30° C. for 5 hr and harvested by centrifugation. Resuspension of the Escherichia coli paste was disrupted by a microfluidizer. FLAG-Tagged protein was purified using FLAG affinity gel (Sigma).

The gel was washed with 20 mmol/L N-(2-hydroxyethyl)piperazine-N'-2-ethanesulfonic acid-sodium hydroxide (HEPES-NaOH), 500 mmol/L sodium chloride, 1% ethylene glycol, and 0.1% polyoxyethylene-polyoxypropylene block copolymer (Pluronic F-68, pH 8.0), and the binding protein was eluted with 20 mmol/L HEPES-NaOH, 100 µg/mL FLAG peptide, 500 mmol/L sodium chloride, 1% ethylene glycol, and 0.1% Pluronic F-68 (pH 8.0).

The eluted fractions containing FLAG-Tagged protein were pooled, dialyzed against 20 mmol/L HEPES-NaOH, 150 mmol/L sodium chloride, 0.5 mmol/L ethylenediamine tetraacetic acid (EDTA), 1% ethylene glycol, and 0.1% Pluronic F-68 (pH 8.0), and preserved at −80° C. Upon the assay, the hPDHK1 enzyme concentration was set at a minimum concentration giving over 90% inhibition of PDH activity.

0.05 U/mL PDH (porcine heart PDH complex, Sigma P7032) and 1.0 μg/mL hPDHK1 were mixed in a buffer (50 mmol/L 3-morpholinopropane sulfonic acid (pH 7.0), 20 mmol/L dipotassium hydrogen phosphate, 60 mmol/L potassium chloride, 2 mmol/L magnesium chloride, 0.4 mmol/L EDTA, 0.2% Pluronic F-68, 2 mmol/L dithiothreitol), and the mixture was incubated at 4° C. overnight to obtain a PDH/hPDHK1 complex.

The test compounds were diluted with dimethyl sulfoxide (DMSO). The PDH/hPDHK1 complex (20 μL), test compound (1.5 μL) and 3.53 μmol/L ATP (diluted with buffer, 8.5 μL) were added to a half area 96 well UV-transparent microplate (Corning 3679), and PDHK reaction was performed at room temperature for 45 min. DMSO (1.5 μL) was added to control wells instead of test compound. In order to determine maximum rate of the PDH reaction, DMSO (1.5 μL) was added to blank wells instead of test compound in absence of hPDHK1.

Then, 10 μL of substrates (5 mmol/L sodium pyruvate, 5 mmol/L Coenzyme A, 12 mmol/L NAD, 5 mmol/L thiamin pyrophosphate, diluted with buffer) were added. The mixture was incubated at room temperature for 90 min, and the residual PDH activity was measured.

The absorbance at 340 nm before and after PDH reaction was measured using a microplate reader to detect NADH produced by the PDH reaction. The hPDHK1 inhibition rate (%) of the test compound was calculated from the formula [{(PDH activity of the test compound−PDH activity of control)/PDH activity of blank−PDH activity of control}×100]. The $IC_{50}$ value was calculated from the concentrations of the test compound at two points enclosing 50% inhibition of the hPDHK1 activity.

The results obtained using compound (2), compound (2h) and compound (3) as test compounds are shown in the following Table 1.

(Inhibitory Action of PDHK2 Activity)

In the case of human PDHK2 (hPDHK2, Genbank Accession No. BC040478.1), modified hPDHK2 cDNA wherein FLAG-Tag sequence was added to the N terminus of hPDHK2 cDNA clone (pReceiver-M01/PDK2-GeneCopoeia) was prepared by PCR and cloned into a vector (pET17b-Novagen). The recombinant construct was transformed into *Escherichia coli* (DH5α-TOYOBO). The recombinant clones were identified, and plasmid DNA was isolated and subjected to the DNA sequence analysis. One clone which had the expected nucleic acid sequence was selected for expression work.

For expression of hPDHK2 activity, *Escherichia coli* strain BL21(DE3) cells (Novagen) were transformed with the pET17b vector containing modified hPDHK2 cDNA. The *Escherichia coli* were grown to an optical density 0.6 (600 nmol/L) at 30° C. Protein expression was induced by the addition of 500 μmol/L isopropyl-β-thiogalactopyranoside. The *Escherichia coli* were cultured at 30° C. for 5 hr and harvested by centrifugation. Resuspension of the *Escherichia coli* paste was disrupted by a microfluidizer. FLAG-Tagged protein was purified using FLAG affinity gel. The gel was washed with 20 mmol/L HEPES-NaOH, 500 mmol/L sodium chloride, 1% ethylene glycol, and 0.1% Pluronic F-68 (pH 8.0), and the binding protein was eluted with 20 mmol/L HEPES-NaOH, 100 μg/mL FLAG peptide, 500 mmol/L sodium chloride, 1% ethylene glycol, and 0.1% Pluronic F-68 (pH 8.0). The eluted fractions containing FLAG-Tagged protein were pooled, dialyzed against 20 mmol/L HEPES-NaOH, 150 mmol/L sodium chloride, 0.5 mmol/L EDTA, 1% ethylene glycol, and 0.1% Pluronic F-68 (pH 8.0), and preserved at −80° C. Upon the assay, the hPDHK2 enzyme concentration was set to a minimum concentration giving over 90% inhibition of PDH activity.

0.05 U/mL PDH and 0.8 μg/mL hPDHK2 were mixed in a buffer (50 mmol/L 3-morpholinopropanesulfonic acid (pH 7.0), 20 mmol/L dipotassium hydrogen phosphate, 60 mmol/L potassium chloride, 2 mmol/L magnesium chloride, 0.4 mmol/L EDTA, and 0.2% Pluronic F-68, 2 mmol/L dithiothreitol), and the mixture was incubated at 4° C. overnight to obtain a PDH/hPDHK2 complex. The test compounds were diluted with DMSO. The PDH/hPDHK2 complex (20 μL), test compound (1.5 μL) and 3.53 μmol/L ATP (diluted with buffer, 8.5 μL) were added to a half area 96 well UV-transparent microplate, and PDHK reaction was performed at room temperature for 45 min. DMSO (1.5 μL) was added to control wells instead of the test compound. In order to determine maximum rate of the PDH reaction, DMSO (1.5 μL) was added to blank wells instead of compound in absence of hPDHK2. Then, 10 μL of substrate (5 mmol/L sodium pyruvate, 5 mmol/L Coenzyme A, 12 mmol/L NAD, and 5 mmol/L thiamine pyrophosphate, diluted with buffer) were added. The mixture was incubated at room temperature for 90 min, and the residual PDH activity was measured. The absorbance at 340 nm before and after PDH reaction was measured using a microplate reader to detect NADH produced by the PDH reaction. The hPDHK2 inhibition rate (%) of the test compound was calculated from the formula [{(PDH activity of test compound−PDH activity of control)/PDH activity of blank−PDH activity of control)}×100]. The $IC_{50}$ value was calculated from the concentrations of the test compound at two points enclosing 50% inhibition of the hPDHK2 activity.

The results obtained using compound (2), compound (2h), compound (3), compound (A), compound (B), compound (C) and compound (D) as test compounds are shown in the following Table 1.

TABLE 1

| Compound | hPDHK1 $IC_{50}$ (μmol/L) | hPDHK2 $IC_{50}$ (μmol/L) |
|---|---|---|
| Compound (2) | 0.0047 | 0.0046 |
| Compound (2h) | 0.0066 | 0.0049 |
| Compound (3) | 0.0035 | 0.0042 |
| Compound (A) | — (not tested) | 0.0051 |
| Compound (B) | — (not tested) | 0.0074 |
| Compound (C) | — (not tested) | 0.0067 |
| Compound (D) | — (not tested) | 0.0051 |

Experimental Example 2

Ex Vivo PDH Activation Assay

Experimental Method

The action of test compound on tissue PDH activity was evaluated. NADH production was detected via p-iodonitrotetrazolium violet (INT)-coupled system to measure PDH activity.

Normal male Sprague-Dawley rats were randomly allocated to the vehicle group and the test compound groups. The vehicle (0.5% aqueous methylcellulose solution, 5 mL/kg) or the test compound was orally administered to the rats. At 5 or 20 hr after administration, the rats were anesthetized with an intraperitoneal injection of sodium pentobarbital (60 mg/kg), and liver slices and epididymal adipose tissues were collected.

To the liver slices were rapidly added 9 volumes of ice-cold homogenization buffer (0.25 mol/L sucrose, 5 mmol/L tris (hydroxymethyl)aminomethane hydrochloride (pH 7.5), 2 mmol/L EDTA), and the mixtures were homogenized using a Polytron homogenizer. The homogenates were centrifuged at 600×g, 4° C. for 10 min to obtain the supernatant. The supernatants (1 mL) were centrifuged at 16,000×g, 4° C. for 10 min to collect the precipitates. The precipitates were washed by resuspension in the homogenization buffer (1 mL) and centrifuged in the same manner. The precipitates were frozen with liquid nitrogen and stored at −80° C. as the liver mitochondrial fraction.

To the adipose tissues were rapidly added 3 volumes of an ice-cold homogenization buffer, and the mixtures were homogenized using a Polytron homogenizer. The homogenates were centrifuged at 600×g, 4° C. for 10 min to obtain the supernatant. The supernatants were centrifuged at 16,000×g, 4° C. for 10 min to collect the precipitates. The precipitates were washed by resuspension in the homogenization buffer (1 mL) and centrifuged in the same manner. The precipitates were frozen with liquid nitrogen and stored at −80° C. as the adipose tissue mitochondrial fraction.

The mitochondrial fractions were thawed and suspended with the sample buffer (0.25 mol/L sucrose, 20 mmol/L tris (hydroxymethyl)aminomethane hydrochloride (pH 7.5), 50 mmol/L potassium chloride, and 1 mL/L 4-(1,1,3,3-tetramethylbutyl)phenyl-polyethylene glycol (Triton X-100)). Active PDH activity (PDHa activity) and total PDH activity (PDHt activity) were measured to evaluate the PDH activity. For the measurement of the PDHt activity, equal amounts of the mitochondrial suspension and the activation buffer (0.25 mol/L sucrose, 20 mmol/L tris(hydroxymethyl)aminomethane hydrochloride (pH 7.5), 50 mmol/L potassium chloride, 1 mL/L Triton X-100, 4 mmol/L calcium chloride, 40 mmol/L magnesium chloride, 10 mmol/L sodium dichloroacetate) were mixed, and the mixtures were incubated at 37° C. for 10 min. Forty microliters of the mitochondrial suspensions diluted with a sample buffer were added to a 96-well microplate for activity measurement and blank measurement. Then 180 μL of the reaction mixture (0.056 mmol/L potassium phosphate buffer (pH 7.5), 5.6 mmol/L DL-carnitine, 2.8 mmol/L NAD, 0.22 mmol/L thiamin pyrophosphate, 0.11 mmol/L Coenzyme A, 1.1 mL/L Triton X-100, 1.1 mmol/L magnesium chloride, 1.1 g/L bovine serum albumin, 0.67 mmol/L INT, 7.2 μmol/L phenazine methosulfate, 28 mmol/L sodium oxamate) was added to each well, and then 20 μL of 50 mmol/L sodium pyruvate for activity measurement or water for blank measurement were added. The mixtures were incubated at room temperature under shading. The absorbances at 500-750 nm, which were attributable to reduction of INT, the final electron acceptor, were measured using a microplate reader over time and the changes in the absorbance were calculated. The PDH activity was calculated by subtraction of the change in absorbance of the blank well from that of the activity measurement well. The percentage of the PDHa activity to the PDHt activity was calculated and taken as an index of the PDH activation.

Figure 2:
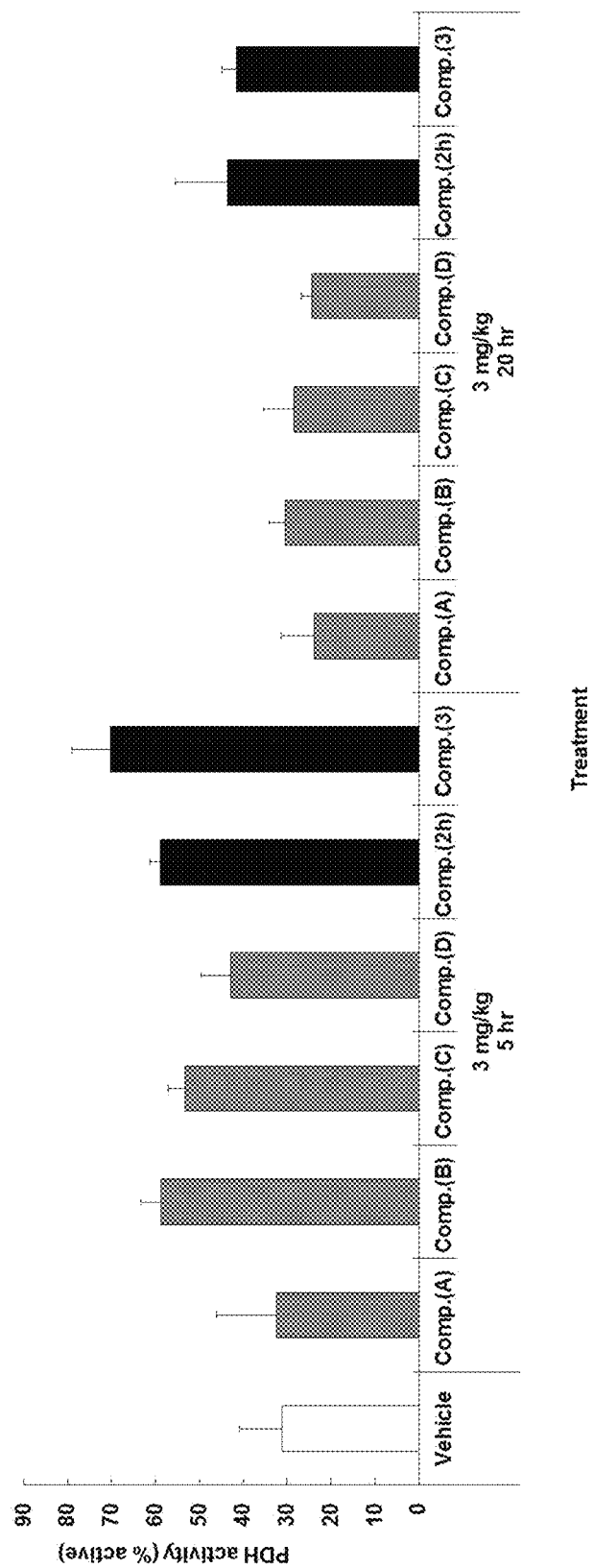
FIG. 2 shows an effect of test compounds on the adipose tissue PDH activity (percentage of active adipose tissue PDH activity to the total adipose tissue PDH activity) in non-fasting SD(IGS) rats (mean±standard deviation (n=3)).

The results obtained using compound (2h), compound (3), compound (A), compound (B), compound (C) and compound (D) as test compounds are shown in the following Table 2, FIG. 1 (Liver) and FIG. 2 (Adipose tissue). In addition, the results obtained using compound (2) are shown in the following Table 3.

TABLE 2

| | PDHa activity (% of PDHt activity) | | | | | | | |
|---|---|---|---|---|---|---|---|---|
| | Liver | | | | Adipose tissue | | | |
| | 5 hr | | 20 hr | | 5 hr | | 20 hr | |
| Compound | Vehicle | 3 mg/kg | Vehicle | 3 mg/kg | Vehicle | 3 mg/kg | Vehicle | 3 mg/kg |
| Compound (2 h) | 13 ± 3 | 59 ± 6 | 13 ± 3 | 31 ± 5 | 31 ± 10 | 59 ± 2 | 31 ± 10 | 44 ± 12 |
| Compound (3) | 13 ± 3 | 56 ± 8 | 13 ± 3 | 32 ± 9 | 31 ± 10 | 70 ± 9 | 31 ± 10 | 42 ± 3 |
| Compound (A) | 13 ± 3 | 35 ± 6 | 13 ± 3 | 16 ± 10 | 31 ± 10 | 32 ± 14 | 31 ± 10 | 24 ± 7 |
| Compound (B) | 13 ± 3 | 43 ± 7 | 13 ± 3 | 10 ± 3 | 31 ± 10 | 59 ± 5 | 31 ± 10 | 30 ± 4 |
| Compound (C) | 13 ± 3 | 44 ± 5 | 13 ± 3 | 13 ± 3 | 31 ± 10 | 53 ± 4 | 31 ± 10 | 28 ± 7 |
| Compound (D) | 13 ± 3 | 41 ± 15 | 13 ± 3 | 20 ± 1 | 31 ± 10 | 43 ± 7 | 31 ± 10 | 24 ± 3 | mean ± S.D. (n = 3)

TABLE 3

| | PDHa activity (% of PDHt activity) | | | | | | | |
|---|---|---|---|---|---|---|---|---|
| | Liver | | | | Adipose tissue | | | |
| | 5 hr | | 20 hr | | 5 hr | | 20 hr | |
| Compound | Vehicle | 3 mg/kg | Vehicle | 3 mg/kg | Vehicle | 3 mg/kg | Vehicle | 3 mg/kg |
| Compound (2) | 28 ± 6 | 74 ± 12 | 28 ± 6 | 50 ± 16 | 42 ± 4 | 88 ± 11 | 42 ± 4 | 61 ± 15 | mean ± S.D. (n = 3)

Experimental Example 3

Effect of Repeated Administration of Test Compound on HbA1c in ZDF Rats

Experimental Method

Zucker Diabetic Fatty rats (male, 7-week-old, CHARLES RIVER LABORATORIES JAPAN INC.), an animal model for type 2 diabetes, given a purified diet (5.9% fat diet, Oriental Yeast Co., Ltd.) were allocated to the vehicle group and the test compound groups so that no bias occurred in the plasma glucose and insulin levels, HbA1c levels and body weights. Repeated oral doses of the test compound (1 mg/kg/5 mL) were administered to the rats once daily at 3 hr before the dark period. A 0.5% aqueous methylcellulose solution was orally administered in the same manner to the rats of the vehicle group. On day 14 of administration, blood samples were collected from the tail vein and HbA1c level (%) was measured. Statistical analysis was performed by Dunnett's test. Values of $p<0.05$ were cosidered statistically significant.

The results obtained using compound (2) and compound (3) as test compounds are shown in the following Table 4.

TABLE 4

| | HbA1c (%) | |
| --- | --- | --- |
| Compound | Vehicle | 1 mg/kg |
| Compound (2) | 3.6 ± 0.3 | 3.2 ± 0.1* |
| Compound (3) | 3.7 ± 0.2 | 3.4 ± 0.1* | day 14 of administration
mean ± S.D. (n = 10)
*p < 0.05 vs. vehicle group (Dunnett's test)

Experimental Example 4 hERG (human Ether-a-go-go Related Gene) Whole Cell Patch Clamp Test

Experimental Method

Using human ether-a-go-go related gene (hERG)-transfected HEK293 cells (Cytomyx Limited), an influence on hERG current was examined according to the whole cell patch clamp technique. The hERG-transfected HEK293 cells were passaged using a $CO_2$ incubator (BNA-111, TABAI ESPEC CORP.) under the set conditions of 37° C., 5% $CO_2$, saturated humidity. Culture containers used were Collagen Type I Coated 75 $cm^2$ flask (4123-010, AGC TECHNO GLASS CO., Ltd.) and Collagen Type I Coated 35 mm culture dish (4000-010, AGC TECHNO GLASS CO., Ltd.). The culture medium used was E-MEM (Eagle Minimum Essential Medium (Earle's Salts, Nikken biomedical laboratory) added with 10% FCS (Fetal calf serum, BioWest, L.L.C.) and 1% MEM Non-Essential Amino Acids Solution (NEAA, Invitrogen Corporation). Geneticin for the selection of hERG gene expressing cells was added thereto to a concentration of 400 μg/mL. As the cells for the measurement, $3 \times 10^4$ hERG-transfected HEK293 cells were plated on a 35 mm culture dish 4 to 7 days before measurement of the hERG current. The culture dish produced for the measurement contained the above-mentioned culture medium without geneticin (Invitrogen Corporation).

The highest evaluation concentration of each compound was determined from the highest concentration at which precipitation was not found in the standard extracellular fluid (NaCl: 140 mmol/L, KCl: 2.5 mmol/L, $MgCl_2$: 2 mmol/L, $CaCl_2$: 2 mmol/L, HEPES: 10 mmol/L, glucose: 10 mmol/L (adjusted to pH 7.4 with Tris-base)). As the application method, each solution to be applied was ejected from a Y-tube having a tip diameter of about 0.25 mm, which was adjacent (about 2 mm) to the cells, and applied to the cells. The ejection rate was about 0.4 mL/min.

The experiment was performed at room temperature under a phase contrast microscope. The 35 mm culture dish plated with the cells was set on a measurement apparatus, and the standard extracellular fluid was continuously applied to the cells from the Y-tube. A glass electrode for the measurement was filled with an intracellular fluid (Potassium Gluconate: 130 mmol/L, KCl: 20 mmol/L, $MgCl_2$: 1 mmol/L, ATP-Mg: 5 mmol/L, EGTA: 3.5 mmol/L, HEPES: 10 mmol/L (adjusted to pH 7.2 with Tris-base)). A conventional whole cell patch clamp method was applied to the cells, and the maintenance electric potential was set to −80 mV. Under a fixed electric potential, the whole cell current was amplified by an amplifier for patch clamp (AXOPATCH-200B, Axon Instruments, Inc.), and the data was loaded into a computer (IMC-P642400, Intermedical Co., Ltd.) using a data acquisition analysis software (pCLAMP 9.2, Axon Instruments, Inc.).

The measurement of the hERG current was performed in the following two steps. In both cases, the hERG current was initiated by giving a command potential (maintenance electric potential −80 mV, prepulse +20 mV, 1.5 sec, test-pulse −50 mV, 1.5 sec).

Step (1): The above-mentioned command potential was given at 0.1 Hz for 2 min.

Step (2): The above-mentioned command potential was subjected to P/3 subtraction of pCLAMP 9.2 to remove leak current. This was repeated three times and an average thereof was taken as hERG current.

Subsequent to step (1), Step (2) was performed (about 3 min), and the maximum tail current obtained by applying a test-pulse to the hERG current obtained by the method of step (2) was taken as hERG current value. Hereafter, the operations of (1) and (2) were alternately repeated until completion of the experiment and the hERG current value was measured.

Stable hERG current value was recorded three times (about 10 min), and the standard extracellular fluid was instantaneously exchanged with each application fluid. The hERG current value was measured three times (about 10 min) in the same manner during perfusion of the application fluid, and the current value obtained by the 3rd measurement was taken as hERG current value after perfusion of the application fluid.

The data for each cell was converted to a relative value with an average of the three hERG current values recorded in about 10 min before perfusion of the application fluid (Before value) as 100%. This was measured for two cells, and an average thereof was calculated as Relative current (%).

Relative current(%)=100×$A \div B$

A: hERG current value after perfusion of application fluid
B: average of three hERG current values recorded in about 10 min before perfusion of application fluid (Before value)

In addition, a suppression rate on the DMSO group was calculated according to the following formula.

Suppression rate(%)=100−($C \div D$)×100

C: average of Relative current (%) of respective test compound groups
D: average of Relative current (%) of DMSO group The results obtained using compound (2), compound (3), compound (A), compound (B), compound (C) and compound (D) as test compounds are shown in the following Table 5.

TABLE 5

| Test compound | Concentration[a] (μmol/L) | Inhibition rate (%) | IC$_{50}$ value (μmol/L) |
|---|---|---|---|
| Compound (2) | 30 | 24.4 | >30 |
| Compound (3) | 30 | 27.3 | >30 |
| Compound (A) | 10 | 11.8 | >10 |
| Compound (B) | 1 | 17.4 | 3.6 |
|  | 10 | 72.9 |  |
| Compound (C) | 3 | 11.5 | 13.2 |
|  | 30 | 69.0 |  |
| Compound (D) | 3 | 9.4 | 14.2 |
|  | 30 | 67.5 |  |

[a]The highest evaluation concentration of each compound was set from the highest concentration at which precipitation in the standard extracellular fluid was not found.

Experimental Example 5

Metabolic Stability Test in Liver Microsome

Experimental Method

Human liver microsome (manufactured by Xenotech, H0620, final concentration (after dilution), 0.2 mg protein/mL) was suspended in 100 mM potassium phosphate buffer (pH 7.4, containing β-nicotinamide adenine dinucleotide phosphate: 1.3 mM, D-glucose-6-phosphate: 3.3 mM, magnesium chloride: 3.3 mM, glucose-6-phosphate dehydrogenase: 0.45 U/mL), and further mixed with a test compound dissolved in MeCN/DMSO (95/5) (final concentration 5 μM). The mixture was incubated at 37° C. for 10 min and 60 min, acetonitrile containing formic acid (final concentration 0.1%) was added, and the mixture was centrifuged. The test compound (unmodified) in the supernatant was measured by high performance liquid chromatography/mass spectrometry (LC/MS) (manufactured by Waters, LC: Acquity UPLC, MS:SQ Detector or TQ Detector). The residual ratio (%) was calculated from the obtained measurement value.

The results obtained using compound (2), compound (3), compound (A), compound (B), compound (C) and compound (D) as test compounds are shown in the following Table 6.

TABLE 6

| | Stability in liver microsome (residual ratio %) | | | |
|---|---|---|---|---|
| | human | | rat | |
| Test compound | 10 min | 60 min | 10 min | 60 min |
| Compound (2) | 98.8 | 96.5 | 98.8 | 100.0 |
| Compound (3) | 98.4 | 85.9 | 102.7 | 95.8 |
| Compound (A) | 34.8 | 0.0 | 24.8 | 0.0 |
| Compound (B) | 98.0 | 88.2 | 101.1 | 92.1 |
| Compound (C) | 94.0 | 75.1 | 94.2 | 85.3 |
| Compound (D) | 105.4 | 101.5 | 105.2 | 105.1 |

INDUSTRIAL APPLICABILITY

Since the compound of the present invention or a pharmaceutically acceptable salt thereof has a PDHK inhibitory activity, it is useful as an active ingredient of a medicament for the prophylaxis or treatment of diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease.

The invention claimed is:
1. A compound represented by the formula [I]:

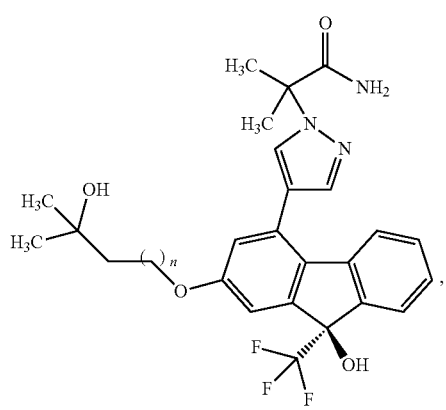

wherein n is 1 or 2,
or a pharmaceutically acceptable salt thereof.
2. A compound represented by the formula:

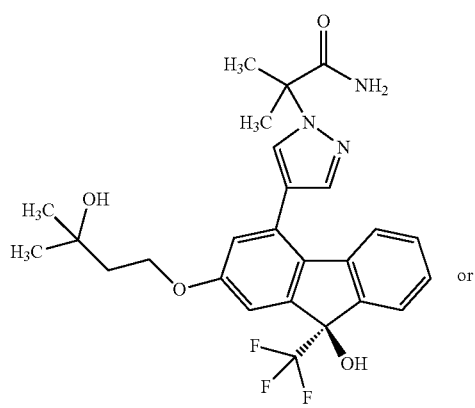

or

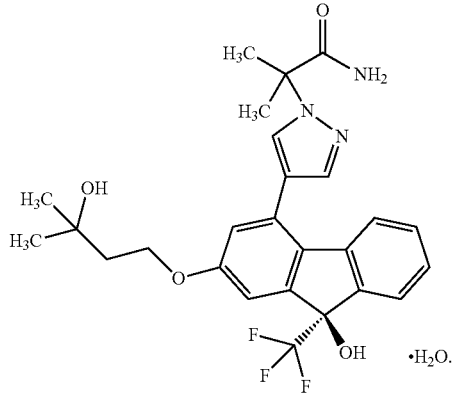

3. The compound according to claim 2, which is represented by the formula [II]:

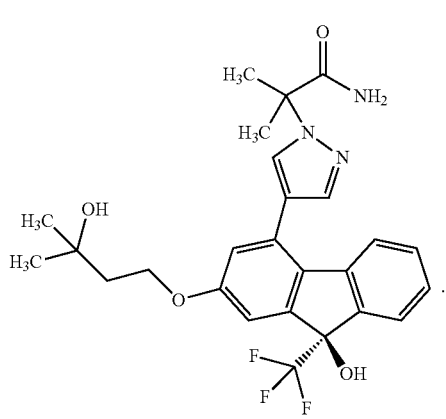

[II]

4. The compound according to claim 2, which is represented by the formula [IIh]:

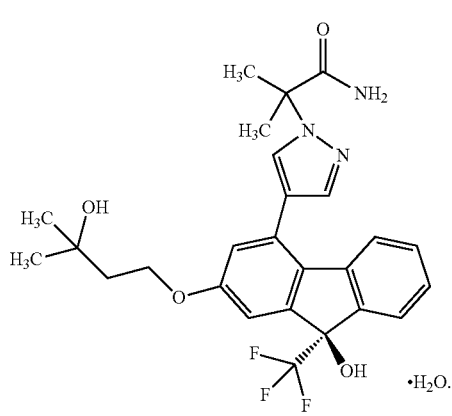

[IIh]

5. A compound represented by the formula [III]:

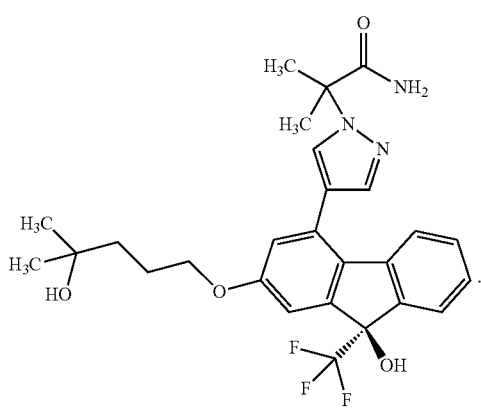

[III]

6. A pharmaceutical composition comprising the compound according to any one of claims 1 to 5, or a pharmaceutically acceptable salt thereof, and a pharmaceutically acceptable carrier.

7. A method for inhibiting PDHK in a mammal comprising administering a pharmaceutically effective amount of the compound according to any one of claims 1 to 5, or a pharmaceutically acceptable salt thereof, to the mammal.

8. A method for inhibiting PDHK1 in a mammal comprising administering a pharmaceutically effective amount of the compound according to any one of claims 1 to 5, or a pharmaceutically acceptable salt thereof, to the mammal.

9. A method for inhibiting PDHK2 in a mammal comprising administering a pharmaceutically effective amount of the compound according to any one of claims 1 to 5, or a pharmaceutically acceptable salt thereof, to the mammal.

10. A method for decreasing the blood glucose level in a mammal comprising administering a pharmaceutically effective amount of the compound according to any one of claims 1 to 5, or a pharmaceutically acceptable salt thereof, to the mammal.

11. A method for decreasing lactate level in a mammal comprising administering a pharmaceutically effective amount of the compound according to any one of claims 1 to 5, or a pharmaceutically acceptable salt thereof, to the mammal.

12. A method for the treatment of diabetes, insulin resistance syndrome, metabolic syndrome, hyperglycemia, hyperlactacidemia, diabetic complications, cardiac failure, cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer or pulmonary hypertension in a mammal, comprising administering a pharmaceutically effective amount of the compound according to any one of claims 1 to 5, or a pharmaceutically acceptable salt thereof, to the mammal.

13. The method according to claim 12, wherein the diabetes is type 1 diabetes or type 2 diabetes.

14. The method according to claim 12, wherein the diabetic complications are selected from the group consisting of diabetic neuropathy, diabetic retinopathy, diabetic nephropathy and cataract.

15. The method according to claim 12, wherein the cardiac failure is acute cardiac failure or chronic cardiac failure.

16. The method according to claim 13, wherein the diabetes is type 2 diabetes.

* * * * *